US011173023B2

(12) United States Patent
Fox et al.

(10) Patent No.: US 11,173,023 B2
(45) Date of Patent: Nov. 16, 2021

(54) MEDICAL DEVICES AND ANCHORS THEREFOR

(71) Applicant: W. L. Gore & Associates, Inc., Newark, DE (US)

(72) Inventors: Aaron D. Fox, Flagstaff, AZ (US); Nicholas S. Webster, Flagstaff, AZ (US); Brett J. Wham, Flagstaff, AZ (US); Roark N. Wolfe, Flagstaff, AZ (US); Peter J. Zeller, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/160,966

(22) Filed: Oct. 15, 2018

(65) Prior Publication Data

US 2019/0110880 A1    Apr. 18, 2019

Related U.S. Application Data

(60) Provisional application No. 62/572,763, filed on Oct. 16, 2017.

(51) Int. Cl.
*A61F 2/01* (2006.01)
*A61B 17/12* (2006.01)
(Continued)

(52) U.S. Cl.
CPC .......... *A61F 2/01* (2013.01); *A61B 17/12031* (2013.01); *A61B 17/12109* (2013.01); *A61B 17/12122* (2013.01); *A61B 17/12172* (2013.01); *A61B 17/12177* (2013.01); *A61F 2/0105* (2020.05); *A61F 2/07* (2013.01);
(Continued)

(58) Field of Classification Search
CPC ........ A61B 17/12031; A61B 17/12109; A61B 17/12122; A61B 17/12172; A61B 17/12177; A61B 2017/00004; A61B 2017/1205; A61F 2002/011; A61F 2210/0004; A61F 2210/0014;
(Continued)

(56) References Cited

U.S. PATENT DOCUMENTS 654,799 A    7/1900  Levett
1,851,314 A  3/1932  Knoche
(Continued)

FOREIGN PATENT DOCUMENTS

CN    1342056 A    3/2002
CN    2820130 Y    9/2006
(Continued)

OTHER PUBLICATIONS

European Search Report for European Application No. 16155556.0 dated Aug. 1, 2016, 10 pages.
(Continued)

*Primary Examiner* — Thomas McEvoy

(57) ABSTRACT

Various aspects of the present disclosure are directed toward apparatuses, systems, and methods for placement in vessels, appendages, and openings in a body including a frame having a proximal end, a distal end, and a longitudinal axis. In certain instances, the frame includes a waist portion angled relative to the longitudinal axis and one or more anchors arranged along the waist portion.

23 Claims, 16 Drawing Sheets

(51) Int. Cl.
*A61F 2/90* (2013.01)
*A61F 2/07* (2013.01)
*A61F 2/962* (2013.01)
*A61B 17/00* (2006.01)

(52) U.S. Cl.
CPC .............. *A61F 2/90* (2013.01); *A61F 2/962* (2013.01); *A61B 2017/00004* (2013.01); *A61B 2017/1205* (2013.01); *A61F 2/011* (2020.05); *A61F 2210/0004* (2013.01); *A61F 2210/0014* (2013.01); *A61F 2220/0008* (2013.01); *A61F 2220/0016* (2013.01)

(58) Field of Classification Search
CPC ...... A61F 2220/0008; A61F 2220/0016; A61F 2/01; A61F 2/07; A61F 2/90; A61F 2/962
See application file for complete search history.

(56) References Cited

U.S. PATENT DOCUMENTS

| | | |
|---|---|---|
| 3,625,451 A | 12/1971 | Anderson |
| 3,915,167 A | 10/1975 | Waterman |
| 3,953,566 A | 4/1976 | Gore |
| 4,222,126 A | 9/1980 | Boretos et al. |
| 4,265,694 A | 5/1981 | Boretos et al. |
| 4,339,831 A | 7/1982 | Johnson |
| 4,340,091 A | 7/1982 | Skelton et al. |
| 4,349,498 A | 9/1982 | Ellis et al. |
| 4,425,908 A | 1/1984 | Simon |
| 4,626,255 A | 12/1986 | Reichart et al. |
| 4,629,459 A | 12/1986 | Ionescu et al. |
| 4,655,246 A | 4/1987 | Philipot et al. |
| 4,692,369 A | 9/1987 | Nomi |
| 4,731,074 A | 3/1988 | Rousseau et al. |
| 4,851,000 A | 7/1989 | Gupta |
| 4,858,810 A | 8/1989 | Intlekofer |
| 4,877,661 A | 10/1989 | House et al. |
| 4,955,899 A | 9/1990 | Della et al. |
| 5,026,513 A | 6/1991 | House et al. |
| 5,071,609 A | 12/1991 | Tu et al. |
| 5,217,486 A | 6/1993 | Rice et al. |
| 5,325,746 A | 7/1994 | Anderson |
| 5,344,427 A | 9/1994 | Cottenceau et al. |
| 5,397,355 A | 3/1995 | Marin |
| 5,476,589 A | 12/1995 | Bacino |
| 5,491,704 A | 2/1996 | Duron |
| 5,527,338 A | 6/1996 | Purdy |
| 5,534,007 A | 7/1996 | St et al. |
| 5,549,663 A | 8/1996 | Cottone, Jr. |
| 5,554,183 A | 9/1996 | Nazari |
| 5,562,726 A | 10/1996 | Chuter |
| 5,693,083 A | 12/1997 | Baker et al. |
| 5,707,376 A | 1/1998 | Kavteladze et al. |
| 5,708,044 A | 1/1998 | Branca |
| 5,709,704 A | 1/1998 | Nott et al. |
| 5,713,917 A | 2/1998 | Leonhardt et al. |
| 5,713,948 A | 2/1998 | Ulfacker |
| 5,718,973 A | 2/1998 | Lewis et al. |
| 5,720,776 A | 2/1998 | Chuter et al. |
| 5,725,552 A | 3/1998 | Kotula |
| 5,759,192 A | 6/1998 | Saunders |
| 5,769,884 A | 6/1998 | Solovay |
| 5,772,884 A | 6/1998 | Tanaka et al. |
| 5,776,141 A | 7/1998 | Klein et al. |
| 5,776,186 A | 7/1998 | Uflacker |
| 5,782,909 A | 7/1998 | Quiachon et al. |
| 5,824,043 A | 10/1998 | Cottone, Jr. |
| 5,824,050 A | 10/1998 | Karwoski et al. |
| 5,843,158 A | 12/1998 | Lenker et al. |
| 5,843,161 A | 12/1998 | Solovay |
| 5,843,162 A | 12/1998 | Inoue |
| 5,904,703 A | 5/1999 | Gilson |
| 5,935,162 A | 8/1999 | Dang |
| 5,961,546 A | 10/1999 | Robinson et al. |
| 6,010,529 A | 1/2000 | Herweck et al. |
| 6,013,093 A | 1/2000 | Nott et al. |
| 6,013,854 A | 1/2000 | Moriuchi |
| 6,015,431 A | 1/2000 | Thornton et al. |
| 6,019,785 A | 2/2000 | Strecker |
| 6,027,779 A | 2/2000 | Campbell et al. |
| 6,042,588 A | 3/2000 | Munsinger et al. |
| 6,042,606 A | 3/2000 | Frantzen |
| 6,143,021 A | 11/2000 | Staeghle |
| 6,152,144 A | 11/2000 | Lesh |
| 6,165,195 A | 12/2000 | Wilson |
| 6,174,331 B1 | 1/2001 | Moe et al. |
| 6,190,406 B1 | 2/2001 | Duerig et al. |
| 6,214,025 B1 | 4/2001 | Thistle et al. |
| 6,224,627 B1 | 5/2001 | Armstrong et al. |
| 6,231,561 B1 | 5/2001 | Frazier et al. |
| 6,231,581 B1 | 5/2001 | Shank et al. |
| 6,231,589 B1 | 5/2001 | Wessman et al. |
| 6,245,012 B1 | 6/2001 | Kleshinski |
| 6,245,939 B1 | 6/2001 | Hsu et al. |
| 6,261,320 B1 | 7/2001 | Tam et al. |
| 6,264,671 B1 | 7/2001 | Stack |
| 6,273,900 B1 | 8/2001 | Nott et al. |
| 6,283,994 B1 | 9/2001 | Moe et al. |
| 6,322,585 B1 | 11/2001 | Khosravi et al. |
| 6,328,727 B1 | 12/2001 | Frazier et al. |
| 6,346,117 B1 | 2/2002 | Greenhalgh |
| 6,352,561 B1 | 3/2002 | Leopold et al. |
| 6,372,870 B1 | 4/2002 | Kitahara et al. |
| 6,436,132 B1 | 8/2002 | Patel et al. |
| 6,451,051 B2 | 9/2002 | Drasler et al. |
| 6,451,396 B1 | 9/2002 | Zumbrum et al. |
| 6,485,513 B1 | 11/2002 | Fan |
| 6,488,701 B1 | 12/2002 | Nolting et al. |
| 6,491,704 B2 | 12/2002 | Gifford, III et al. |
| 6,524,335 B1 | 2/2003 | Hartley et al. |
| 6,527,779 B1 | 3/2003 | Rourke |
| 6,541,589 B1 | 4/2003 | Baillie |
| 6,551,303 B1 | 4/2003 | Van Tessel et al. |
| 6,551,350 B1 | 4/2003 | Thornton et al. |
| 6,562,069 B2 | 5/2003 | Cai et al. |
| 6,572,643 B1 | 6/2003 | Gharibadeh |
| 6,572,646 B1 | 6/2003 | Boylan et al. |
| 6,620,190 B1 | 9/2003 | Colone |
| 6,626,939 B1 | 9/2003 | Burnside et al. |
| 6,652,556 B1 | 11/2003 | Vantassel et al. |
| 6,666,885 B2 | 12/2003 | Moe |
| 6,673,455 B2 | 1/2004 | Zumbrum et al. |
| 6,689,150 B1 | 2/2004 | Van Tassel |
| 6,705,563 B2 | 3/2004 | Luo et al. |
| 6,712,836 B1 | 3/2004 | Berg et al. |
| 6,712,842 B1 | 3/2004 | Gifford, III et al. |
| 6,726,715 B2 | 4/2004 | Sutherland |
| 6,730,108 B2 | 5/2004 | Van Tassel |
| 6,730,120 B2 | 5/2004 | Berg et al. |
| 6,743,210 B2 | 6/2004 | Hart et al. |
| 6,746,472 B2 | 6/2004 | Frazier et al. |
| 6,755,854 B2 | 6/2004 | Gillick et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,770,579 B1 | 8/2004 | Dawson et al. |
| 6,776,604 B1 | 8/2004 | Chobotov et al. |
| 6,827,731 B2 | 12/2004 | Armstrong et al. |
| 6,866,669 B2 | 3/2005 | Buzzard et al. |
| 6,884,259 B2 | 4/2005 | Tran et al. |
| 6,926,732 B2 | 8/2005 | Derus et al. |
| 6,939,352 B2 | 9/2005 | Buzzard et al. |
| 6,945,990 B2 | 9/2005 | Greenan |
| 6,949,113 B2 | 9/2005 | Van Tassel |
| 6,953,332 B1 | 10/2005 | Kurk et al. |
| 6,974,471 B2 | 12/2005 | Van Shie et al. |
| 6,994,092 B2 | 2/2006 | Van Der Burg et al. |
| 7,033,368 B2 | 4/2006 | Rourke |
| 7,044,134 B2 | 5/2006 | Khairkhahan |
| 7,049,380 B1 | 5/2006 | Chang |
| 7,052,511 B2 | 5/2006 | Weldon et al. |
| 7,066,951 B2 | 6/2006 | Chovotov |
| 7,083,642 B2 | 8/2006 | Sirhan et al. |

(56) References Cited

U.S. PATENT DOCUMENTS

| | | |
|---|---|---|
| 7,105,018 B1 | 9/2006 | Yip et al. |
| 7,122,050 B2 | 10/2006 | Randall et al. |
| 7,128,073 B1 | 10/2006 | Van Der Burg et al. |
| 7,147,657 B2 | 12/2006 | Chiang et al. |
| 7,169,160 B1 | 1/2007 | Middleman et al. |
| 7,198,636 B2 | 4/2007 | Cully et al. |
| 7,208,003 B2 | 4/2007 | Davis et al. |
| 7,238,200 B2 | 7/2007 | Lee et al. |
| 7,252,680 B2 | 8/2007 | Freitag |
| 7,306,729 B2 | 12/2007 | Bacino et al. |
| 7,331,992 B2 | 2/2008 | Randall et al. |
| 7,396,359 B1 | 7/2008 | DeRowe |
| 7,419,678 B2 | 9/2008 | Falotico |
| 7,448,122 B1 | 11/2008 | Kokish et al. |
| 7,462,675 B2 | 12/2008 | Chang et al. |
| 7,531,611 B2 | 5/2009 | Sabol et al. |
| 7,555,034 B2 | 6/2009 | Shin et al. |
| 7,566,336 B2 | 7/2009 | Corcoran et al. |
| 7,572,289 B2 | 8/2009 | Sisken et al. |
| 7,601,159 B2 | 10/2009 | Ewers et al. |
| 7,611,528 B2 | 11/2009 | Goodson et al. |
| 7,628,803 B2 | 12/2009 | Pavcnik et al. |
| 7,655,034 B2 | 2/2010 | Mitchell et al. |
| 7,678,123 B2 | 3/2010 | Chanduszko |
| 7,771,455 B2 | 8/2010 | Ken |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,591 B2 | 10/2010 | Levine et al. |
| 7,815,763 B2 | 10/2010 | Fierens et al. |
| 7,833,565 B2 | 11/2010 | O'Connor et al. |
| 7,846,179 B2 | 12/2010 | Belef et al. |
| 7,887,580 B2 | 2/2011 | Randall et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,976,575 B2 | 7/2011 | Hartley |
| 7,998,189 B2 | 8/2011 | Kolbel et al. |
| 8,029,557 B2 | 10/2011 | Sobrino-Serrano et al. |
| 8,029,559 B2 | 10/2011 | Sisken et al. |
| 8,029,563 B2 | 10/2011 | House et al. |
| 8,048,440 B2 | 11/2011 | Chang |
| 8,062,349 B2 | 11/2011 | Moore et al. |
| 8,080,032 B2 | 12/2011 | van der Burg |
| 8,157,810 B2 | 4/2012 | Case et al. |
| 8,167,935 B2 | 5/2012 | McGuckin et al. |
| 8,231,650 B2 | 7/2012 | Cully |
| 8,241,350 B2 | 8/2012 | Randall et al. |
| 8,273,105 B2 | 9/2012 | Cohen et al. |
| 8,287,583 B2 | 10/2012 | LaDuca et al. |
| 8,349,000 B2 | 1/2013 | Schreck |
| 8,424,166 B2 | 4/2013 | Dorneman et al. |
| 8,449,595 B2 | 5/2013 | Ouellette et al. |
| 8,469,990 B2 | 6/2013 | McGuckin |
| 8,475,512 B2 | 7/2013 | Hunt |
| 8,523,897 B2 | 9/2013 | van der Burg |
| 8,529,597 B2 | 9/2013 | Linder |
| 8,585,757 B2 | 11/2013 | Agathos |
| 8,637,144 B2 | 1/2014 | Ford |
| 8,685,055 B2 | 4/2014 | Van Tassel |
| 8,709,077 B2 | 4/2014 | Schreck |
| 8,801,746 B1 | 8/2014 | Kreidler |
| 8,834,519 B2 | 9/2014 | van der Burg |
| 8,870,947 B2 | 10/2014 | Shaw |
| 8,945,212 B2 | 2/2015 | Bruchman et al. |
| 8,961,599 B2 | 2/2015 | Bruchman et al. |
| 9,109,310 B2 | 8/2015 | Baaijens et al. |
| 9,254,204 B2 | 2/2016 | Roeder |
| 9,314,249 B2 | 4/2016 | Kreidler |
| 9,504,565 B2 | 11/2016 | Armstrong |
| 9,554,806 B2 | 1/2017 | Larsen et al. |
| 9,554,900 B2 | 1/2017 | Bruchman et al. |
| 9,597,086 B2 | 3/2017 | Larsen et al. |
| 9,743,932 B2 | 8/2017 | Amplatz |
| 9,744,033 B2 | 8/2017 | Bruchman et al. |
| 9,770,327 B2 | 9/2017 | Bruchman et al. |
| 9,795,475 B2 | 10/2017 | Bruchman et al. |
| 9,801,712 B2 | 10/2017 | Bruchman et al. |
| 10,022,219 B2 | 7/2018 | Bruchman et al. |
| 10,342,658 B2 | 7/2019 | Bruchman et al. |
| 10,470,878 B2 | 11/2019 | Bruchman et al. |
| 2001/0037142 A1 | 11/2001 | Stelter et al. |
| 2001/0051824 A1 | 12/2001 | Hopkins et al. |
| 2002/0007208 A1 | 1/2002 | Strecker et al. |
| 2002/0029077 A1 | 3/2002 | Leopold et al. |
| 2002/0045936 A1 | 4/2002 | Moe |
| 2002/0055773 A1 | 5/2002 | Campbell et al. |
| 2002/0091439 A1 | 7/2002 | Baker et al. |
| 2002/0099431 A1 | 7/2002 | Armstrong et al. |
| 2002/0151953 A1 | 10/2002 | Chobotov et al. |
| 2002/0198588 A1 | 12/2002 | Armstrong et al. |
| 2002/0198594 A1 | 12/2002 | Schreck |
| 2003/0004559 A1 | 1/2003 | Lentz et al. |
| 2003/0004560 A1 | 1/2003 | Chobotov et al. |
| 2003/0012905 A1 | 1/2003 | Zumbrum et al. |
| 2003/0023303 A1 | 1/2003 | Palmaz et al. |
| 2003/0040771 A1 | 2/2003 | Hyodoh et al. |
| 2003/0055492 A1 | 3/2003 | Shaolian et al. |
| 2003/0055495 A1 | 3/2003 | Pease et al. |
| 2003/0055496 A1 | 3/2003 | Cai et al. |
| 2003/0057156 A1 | 3/2003 | Peterson et al. |
| 2003/0060871 A1 | 3/2003 | Hill et al. |
| 2003/0097175 A1 | 5/2003 | O'Connor et al. |
| 2003/0098383 A1 | 5/2003 | Luo et al. |
| 2003/0114917 A1 | 6/2003 | Holloway et al. |
| 2003/0139806 A1 | 7/2003 | Haverkost et al. |
| 2003/0149467 A1 | 8/2003 | Linder et al. |
| 2003/0181942 A1 | 9/2003 | Sutton |
| 2003/0211264 A1 | 11/2003 | Farnsworth et al. |
| 2003/0229394 A1 | 12/2003 | Ogle et al. |
| 2004/0019374 A1 | 1/2004 | Hojeibane et al. |
| 2004/0024442 A1 | 2/2004 | Sowinski et al. |
| 2004/0024448 A1 | 2/2004 | Chang et al. |
| 2004/0034366 A1 | 2/2004 | Van der Burg et al. |
| 2004/0044361 A1 | 3/2004 | Frazier et al. |
| 2004/0054396 A1 | 3/2004 | Hartley |
| 2004/0073289 A1 | 4/2004 | Hartley |
| 2004/0093070 A1 | 5/2004 | Hojeibane et al. |
| 2004/0122503 A1 | 6/2004 | Campbell et al. |
| 2004/0138734 A1 | 7/2004 | Chobotov et al. |
| 2004/0143315 A1 | 7/2004 | Bruun et al. |
| 2004/0167619 A1 | 8/2004 | Case et al. |
| 2004/0176839 A1 | 9/2004 | Huynh et al. |
| 2004/0260393 A1 | 12/2004 | Rahdert et al. |
| 2005/0038470 A1 | 2/2005 | Van Der Burg et al. |
| 2005/0049667 A1 | 3/2005 | Arbefeuille et al. |
| 2005/0070820 A1 | 3/2005 | Boutillette |
| 2005/0080476 A1 | 4/2005 | Gunderson et al. |
| 2005/0085890 A1 | 4/2005 | Rasmussen |
| 2005/0113861 A1 | 5/2005 | Corcoran |
| 2005/0125031 A1 | 6/2005 | Pipenhagen et al. |
| 2005/0137682 A1 | 6/2005 | Justino |
| 2005/0240257 A1 | 10/2005 | Ishimaru et al. |
| 2005/0261765 A1 | 11/2005 | Liddicoat |
| 2005/0283224 A1 | 12/2005 | King |
| 2005/0288767 A1 | 12/2005 | Kujawski et al. |
| 2006/0004433 A1 | 1/2006 | Greenberg et al. |
| 2006/0015171 A1 | 1/2006 | Armstrong |
| 2006/0036311 A1 | 2/2006 | Nakayama et al. |
| 2006/0058833 A1 | 3/2006 | Vancamp |
| 2006/0058889 A1 | 3/2006 | Case et al. |
| 2006/0135947 A1 | 6/2006 | Soltesz et al. |
| 2006/0155366 A1 | 7/2006 | LaDuca et al. |
| 2006/0190074 A1 | 8/2006 | Hill et al. |
| 2006/0254569 A1 | 11/2006 | Chipman |
| 2006/0259133 A1 | 11/2006 | Sowinski et al. |
| 2006/0264980 A1 | 11/2006 | Khairkhahan et al. |
| 2006/0265053 A1 | 11/2006 | Hunt |
| 2006/0276883 A1 | 12/2006 | Greenberg et al. |
| 2006/0276888 A1 | 12/2006 | Lee et al. |
| 2006/0290027 A1 | 12/2006 | O'Connor et al. |
| 2007/0012624 A1 | 1/2007 | Bacino et al. |
| 2007/0027528 A1 | 2/2007 | Agnew |

(56) References Cited

U.S. PATENT DOCUMENTS

| | | |
|---|---|---|
| 2007/0027535 A1 | 2/2007 | Purdy et al. |
| 2007/0060999 A1 | 3/2007 | Randall et al. |
| 2007/0066993 A1 | 3/2007 | Kreidler |
| 2007/0067021 A1 | 3/2007 | Haverkost et al. |
| 2007/0088424 A1 | 4/2007 | Greenberg |
| 2007/0100427 A1 | 5/2007 | Perouse |
| 2007/0118209 A1 | 5/2007 | Strecker |
| 2007/0118210 A1 | 5/2007 | Pinchuk |
| 2007/0129786 A1 | 6/2007 | Beach et al. |
| 2007/0162048 A1 | 7/2007 | Quinn et al. |
| 2007/0167955 A1 | 7/2007 | Arnault de la Menardiere et al. |
| 2007/0198077 A1 | 8/2007 | Cully et al. |
| 2007/0198078 A1 | 8/2007 | Berra et al. |
| 2007/0208421 A1 | 9/2007 | Quigley |
| 2007/0213800 A1 | 9/2007 | Fierens et al. |
| 2007/0219467 A1 | 9/2007 | Clark |
| 2007/0248640 A1 | 10/2007 | Karabey et al. |
| 2007/0249980 A1 | 10/2007 | Carrez et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2007/0255390 A1 | 11/2007 | Ducke et al. |
| 2007/0270891 A1 | 11/2007 | McGuckin |
| 2007/0288087 A1 | 12/2007 | Fearnot et al. |
| 2008/0027529 A1 | 1/2008 | Hartley et al. |
| 2008/0178434 A1 | 1/2008 | Bulanda |
| 2008/0033527 A1 | 2/2008 | Nunez et al. |
| 2008/0033534 A1 | 2/2008 | Cook |
| 2008/0039925 A1 | 2/2008 | Ishimaru et al. |
| 2008/0051876 A1 | 2/2008 | Ta et al. |
| 2008/0091261 A1 | 4/2008 | Long et al. |
| 2008/0114440 A1 | 5/2008 | Hlavka et al. |
| 2008/0119943 A1 | 5/2008 | Armstrong et al. |
| 2008/0125711 A1 | 5/2008 | Alpini et al. |
| 2008/0133004 A1 | 6/2008 | White |
| 2008/0147111 A1 | 6/2008 | Johnson |
| 2008/0200977 A1 | 8/2008 | Paul et al. |
| 2008/0208329 A1 | 8/2008 | Bishop |
| 2008/0269785 A1 | 10/2008 | Lampropoulos |
| 2008/0319531 A1 | 12/2008 | Doran et al. |
| 2009/0004239 A1 | 1/2009 | Ladet et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0048656 A1 | 2/2009 | Wen |
| 2009/0054723 A1 | 2/2009 | Khairkhahan et al. |
| 2009/0062838 A1 | 3/2009 | Brumleve et al. |
| 2009/0082844 A1 | 3/2009 | Zacharias et al. |
| 2009/0099596 A1 | 4/2009 | McGuckin, Jr. |
| 2009/0099640 A1 | 4/2009 | Weng |
| 2009/0112249 A1 | 4/2009 | Miles |
| 2009/0157175 A1 | 6/2009 | Benichou |
| 2009/0171386 A1 | 7/2009 | Amplatz |
| 2009/0182413 A1 | 7/2009 | Burkart et al. |
| 2009/0187197 A1 | 7/2009 | Roeber et al. |
| 2009/0216308 A1 | 8/2009 | Hartley |
| 2009/0216321 A1 | 8/2009 | Osborne et al. |
| 2009/0259291 A1 | 10/2009 | Kolbel et al. |
| 2010/0011564 A1 | 1/2010 | Millwee et al. |
| 2010/0016943 A1 | 1/2010 | Chobotov |
| 2010/0023048 A1 | 1/2010 | Mach |
| 2010/0023114 A1 | 1/2010 | Chambers et al. |
| 2010/0057195 A1 | 3/2010 | Roeder et al. |
| 2010/0094394 A1 | 4/2010 | Beach et al. |
| 2010/0094401 A1 | 4/2010 | Kolbel |
| 2010/0094405 A1 | 4/2010 | Cottone |
| 2010/0106240 A1 | 4/2010 | Duggal et al. |
| 2010/0159171 A1 | 6/2010 | Clough |
| 2010/0190254 A1 | 7/2010 | Chian et al. |
| 2010/0211052 A1 | 8/2010 | Brown et al. |
| 2010/0248324 A1 | 9/2010 | Xu et al. |
| 2010/0249922 A1 | 9/2010 | Li et al. |
| 2010/0280591 A1 | 11/2010 | Shin |
| 2011/0039690 A1 | 2/2011 | Niu |
| 2011/0040366 A1 | 2/2011 | Goetz et al. |
| 2011/0049757 A1 | 3/2011 | O'Connor et al. |
| 2011/0054515 A1 | 3/2011 | Bridgeman |
| 2011/0054519 A1 | 3/2011 | Neuss |
| 2011/0064781 A1 | 3/2011 | Cleek et al. |
| 2011/0066221 A1 | 3/2011 | White et al. |
| 2011/0125252 A1 | 5/2011 | Goddard |
| 2011/0130821 A1 | 6/2011 | Styrc |
| 2011/0142804 A1 | 6/2011 | Gaudette et al. |
| 2011/0218619 A1 | 9/2011 | Benichou et al. |
| 2011/0250689 A1 | 10/2011 | Baaijens et al. |
| 2011/0311746 A1 | 12/2011 | Ma et al. |
| 2011/0313503 A1 | 12/2011 | Berra et al. |
| 2012/0022630 A1 | 1/2012 | Wubbeling |
| 2012/0022638 A1 | 1/2012 | Leewood et al. |
| 2012/0046652 A1 | 2/2012 | Sokel |
| 2012/0058100 A1 | 3/2012 | Shastri et al. |
| 2012/0061314 A1 | 3/2012 | Choi et al. |
| 2012/0065667 A1 | 3/2012 | Javois et al. |
| 2012/0078357 A1 | 3/2012 | Conklin |
| 2012/0116496 A1 | 5/2012 | Chuter et al. |
| 2012/0123529 A1 | 5/2012 | Levi et al. |
| 2012/0123530 A1 | 5/2012 | Carpentier et al. |
| 2012/0129150 A1 | 5/2012 | Carbonell |
| 2012/0130473 A1 | 5/2012 | Norris et al. |
| 2012/0130474 A1 | 5/2012 | Buckley |
| 2012/0130475 A1 | 5/2012 | Shaw |
| 2012/0143242 A1 | 6/2012 | Masters |
| 2012/0143305 A1 | 6/2012 | Berra et al. |
| 2012/0172927 A1 | 7/2012 | Cambell et al. |
| 2012/0172965 A1 | 7/2012 | Kratzberg et al. |
| 2012/0172968 A1 | 7/2012 | Chuter et al. |
| 2012/0253450 A1 | 10/2012 | Case et al. |
| 2012/0253453 A1 | 10/2012 | Bruchman et al. |
| 2012/0283585 A1 | 11/2012 | Werneth et al. |
| 2012/0283773 A1 | 11/2012 | Van Tassel |
| 2012/0290082 A1 | 11/2012 | Quint et al. |
| 2012/0296360 A1 | 11/2012 | Norris et al. |
| 2012/0296418 A1 | 11/2012 | Bonyuet et al. |
| 2012/0323211 A1 | 12/2012 | Ogle et al. |
| 2012/0323270 A1 | 12/2012 | Lee |
| 2012/0323315 A1 | 12/2012 | Bruchman et al. |
| 2013/0023981 A1 | 1/2013 | Dierking et al. |
| 2013/0046371 A1 | 2/2013 | Greenberg et al. |
| 2013/0073029 A1 | 3/2013 | Shaw |
| 2013/0123896 A1 | 5/2013 | Bloss et al. |
| 2013/0123908 A1 | 5/2013 | Hinchliffe et al. |
| 2013/0138138 A1 | 5/2013 | Clark |
| 2013/0150947 A1 | 6/2013 | Kaufmann et al. |
| 2013/0158647 A1 | 6/2013 | Norris et al. |
| 2013/0166021 A1 | 6/2013 | Bruchman et al. |
| 2013/0178889 A1 | 7/2013 | Miles |
| 2013/0184807 A1 | 7/2013 | Kovach et al. |
| 2013/0197631 A1 | 8/2013 | Bruchman et al. |
| 2013/0245666 A1 | 9/2013 | Larsen et al. |
| 2013/0245742 A1 | 9/2013 | Norris |
| 2013/0296912 A1 | 11/2013 | Ottma |
| 2013/0310924 A1 | 11/2013 | Groothuis et al. |
| 2013/0331929 A1 | 12/2013 | Mitra et al. |
| 2014/0005773 A1 | 1/2014 | Wheatley |
| 2014/0012303 A1 | 1/2014 | Heipl |
| 2014/0018841 A1 | 1/2014 | Peiffer |
| 2014/0031927 A1 | 1/2014 | Bruchman et al. |
| 2014/0046360 A1 | 2/2014 | van der Burg |
| 2014/0135817 A1 | 5/2014 | Tischler |
| 2014/0135897 A1 | 5/2014 | Cully et al. |
| 2014/0142617 A1 | 5/2014 | Larsen |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172080 A1 | 6/2014 | Bruchman et al. |
| 2014/0172081 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0188220 A1 | 7/2014 | Seguin |
| 2014/0253453 A1 | 9/2014 | Lo |
| 2014/0288642 A1 | 9/2014 | Yoshida et al. |

(56) References Cited

U.S. PATENT DOCUMENTS

| | | | |
|---|---|---|---|
| 2014/0296908 A1 | 10/2014 | Ottma | |
| 2014/0296909 A1 | 10/2014 | Heipl | |
| 2014/0350592 A1* | 11/2014 | Kreidler | A61B 17/1215 606/200 |
| 2014/0379019 A1 | 12/2014 | Larsen | |
| 2015/0005809 A1 | 1/2015 | Ayres et al. | |
| 2015/0005810 A1 | 1/2015 | Center | |
| 2015/0051695 A1 | 2/2015 | Shaw | |
| 2015/0135537 A1 | 5/2015 | Bruchman et al. | |
| 2015/0223757 A1 | 8/2015 | Werneth et al. | |
| 2015/0224231 A1 | 8/2015 | Bruchman et al. | |
| 2015/0257875 A1 | 9/2015 | Bruchman et al. | |
| 2015/0257876 A1 | 9/2015 | Bruchman et al. | |
| 2015/0257882 A1* | 9/2015 | Bortlein | A61F 2/2418 623/2.11 |
| 2015/0265744 A1 | 9/2015 | Baaijens | |
| 2015/0283297 A1 | 10/2015 | Baaijens et al. | |
| 2015/0305749 A1 | 10/2015 | Alferness | |
| 2015/0305862 A1 | 10/2015 | Bruchman et al. | |
| 2015/0306277 A1 | 10/2015 | Pathak et al. | |
| 2015/0351904 A1* | 12/2015 | Cooper | A61F 2/2418 623/2.1 |
| 2015/0366663 A1 | 12/2015 | Bruchman et al. | |
| 2016/0008133 A9 | 1/2016 | Day et al. | |
| 2016/0067374 A1 | 3/2016 | Puckett et al. | |
| 2016/0074161 A1 | 3/2016 | Bennett | |
| 2016/0100939 A1 | 4/2016 | Armstrong et al. | |
| 2016/0175095 A1 | 6/2016 | Dienno et al. | |
| 2016/0175096 A1 | 6/2016 | Dienno et al. | |
| 2016/0317299 A1 | 11/2016 | Alkhatib | |
| 2016/0331382 A1 | 11/2016 | Center | |
| 2017/0042674 A1 | 2/2017 | Armstrong | |
| 2017/0181751 A1 | 6/2017 | Larsen | |
| 2017/0319338 A1 | 11/2017 | Bruchman et al. | |
| 2018/0008406 A1 | 1/2018 | Bruchman et al. | |
| 2018/0200050 A1 | 7/2018 | Bruchman et al. | |
| 2019/0110880 A1 | 4/2019 | Fox et al. | |
| 2019/0114303 A1 | 4/2019 | Peloski | |
| 2019/0258641 A1 | 8/2019 | Peloski | |
| 2019/0269506 A1 | 9/2019 | Bruchman et al. | |
| 2021/0038230 A1 | 2/2021 | Larsen et al. | |

FOREIGN PATENT DOCUMENTS

| | | |
|---|---|---|
| CN | 2904980 Y | 5/2007 |
| CN | 101304693 A | 11/2008 |
| CN | 101554343 | 10/2009 |
| CN | 101780306 | 7/2010 |
| CN | 101965161 | 2/2011 |
| CN | 201879866 U | 6/2011 |
| CN | 201930098 U | 8/2011 |
| CN | 102908174 | 2/2013 |
| CN | 103347467 | 10/2013 |
| DE | 102014102725 | 9/2015 |
| EP | 0150608 A1 | 8/1985 |
| EP | 0293090 A2 | 11/1988 |
| EP | 0313263 A2 | 4/1989 |
| EP | 0664107 A1 | 7/1995 |
| EP | 0679372 A2 | 11/1995 |
| EP | 0815806 A2 | 1/1998 |
| EP | 0893108 A2 | 1/1999 |
| EP | 0773971 B1 | 6/1999 |
| EP | 1318775 A1 | 6/2003 |
| EP | 1977719 A2 | 10/2008 |
| EP | 2074953 A1 | 7/2009 |
| EP | 2481381 | 8/2012 |
| EP | 2596754 A1 | 5/2013 |
| FR | 2896405 | 7/2007 |
| GB | 2344054 A | 5/2000 |
| JP | 02-000645 A | 1/1990 |
| JP | 1996126704 | 5/1996 |
| JP | 09-501759 A | 2/1997 |
| JP | 09-241412 A | 9/1997 |
| JP | 2001506902 | 7/1998 |
| JP | 11-290448 A | 10/1999 |
| JP | 2002503114 | 1/2002 |
| JP | 2002518086 | 6/2002 |
| JP | 2004-510471 A | 4/2004 |
| JP | 2004167239 | 6/2004 |
| JP | 2004188219 | 7/2004 |
| JP | 2005-505320 A | 2/2005 |
| JP | 2005-530549 A | 10/2005 |
| JP | 2007502689 | 2/2007 |
| JP | 2007518465 | 7/2007 |
| JP | 2008-506459 A | 3/2008 |
| JP | 2008-531117 A | 8/2008 |
| JP | 2009-542421 A | 12/2009 |
| JP | 2010527742 | 8/2010 |
| JP | 2010-535075 A | 11/2010 |
| JP | 2011-005292 A | 1/2011 |
| JP | 2011509117 | 3/2011 |
| JP | 2011511693 | 4/2011 |
| JP | 2011516202 | 5/2011 |
| JP | 2013-545515 A | 12/2013 |
| JP | 2014501563 | 1/2014 |
| JP | 2014501565 | 1/2014 |
| JP | 2014502180 | 1/2014 |
| JP | 2014-533970 A | 12/2014 |
| JP | 2014533189 | 12/2014 |
| JP | 2015-534881 A | 12/2015 |
| RU | 2124986 C1 | 1/1999 |
| WO | 95/05555 A1 | 2/1995 |
| WO | 95/28899 A1 | 11/1995 |
| WO | WO-1996018361 A1 | 6/1996 |
| WO | 97/10871 A1 | 3/1997 |
| WO | WO-1997048350 A1 | 12/1997 |
| WO | 98/26731 A2 | 6/1998 |
| WO | WO-1999065420 A1 | 12/1999 |
| WO | WO-2000013613 A1 | 3/2000 |
| WO | 00/41649 A1 | 7/2000 |
| WO | 00/62716 A1 | 10/2000 |
| WO | WO-2001021109 A1 | 3/2001 |
| WO | 01/30266 A1 | 5/2001 |
| WO | 01/74272 A2 | 10/2001 |
| WO | 02/24118 A1 | 3/2002 |
| WO | 02/24119 A1 | 3/2002 |
| WO | WO-2002028317 A2 | 4/2002 |
| WO | 02/60506 A1 | 8/2002 |
| WO | 2002/100454 A1 | 12/2002 |
| WO | 03/47468 A1 | 6/2003 |
| WO | 2004/000375 A1 | 12/2003 |
| WO | WO-2007092354 A2 | 8/2004 |
| WO | WO-2008063464 A2 | 5/2005 |
| WO | WO-2005072652 | 8/2005 |
| WO | 2006/000763 A2 | 1/2006 |
| WO | WO-2006007389 A1 | 1/2006 |
| WO | 2006/019626 A2 | 2/2006 |
| WO | 2006/091382 A1 | 8/2006 |
| WO | 2006/127756 A2 | 11/2006 |
| WO | 2007/002320 A1 | 1/2007 |
| WO | 2007/016251 A2 | 2/2007 |
| WO | 2008/006003 A2 | 1/2008 |
| WO | 2008/028964 A2 | 3/2008 |
| WO | 2008/036870 A2 | 3/2008 |
| WO | 2008/049045 A2 | 4/2008 |
| WO | WO-2008047092 A2 | 4/2008 |
| WO | 2009/017827 A1 | 2/2009 |
| WO | 2009/038761 A1 | 3/2009 |
| WO | 2009/045332 A2 | 4/2009 |
| WO | WO-2009088905 | 7/2009 |
| WO | 2009/100210 A1 | 8/2009 |
| WO | WO-2009102441 A1 | 8/2009 |
| WO | WO-2009126227 A2 | 10/2009 |
| WO | 2009/149462 A2 | 12/2009 |
| WO | WO-2009148594 A1 | 12/2009 |
| WO | 2010/006783 A1 | 1/2010 |
| WO | WO-2010001012 A1 | 1/2010 |
| WO | 2010/030766 A1 | 3/2010 |
| WO | WO-2010024881 | 3/2010 |
| WO | WO-2010041038 A1 | 4/2010 |
| WO | WO-2010044854 A1 | 4/2010 |
| WO | WO-2010063795 A1 | 6/2010 |
| WO | WO-2010081041 | 7/2010 |

(56) References Cited

FOREIGN PATENT DOCUMENTS

| WO | WO-2010090699 A1 | 8/2010 |
|---|---|---|
| WO | WO-2010105195 A2 | 9/2010 |
| WO | 2010/132707 A1 | 11/2010 |
| WO | WO-2011031981 | 3/2011 |
| WO | WO-2011062858 A1 | 5/2011 |
| WO | 2011/065809 A2 | 6/2011 |
| WO | WO-2012068257 A2 | 5/2012 |
| WO | 2012/109297 A2 | 8/2012 |
| WO | 2012/135603 A2 | 10/2012 |
| WO | 2012/163257 A1 | 12/2012 |
| WO | 2012/167131 A1 | 12/2012 |
| WO | WO-2013040431 A1 | 3/2013 |
| WO | WO-2013137977 A1 | 9/2013 |
| WO | 2014/036439 A2 | 3/2014 |
| WO | 2014/078078 A1 | 5/2014 |
| WO | 2014/078531 A1 | 5/2014 |
| WO | 2014/210263 A1 | 12/2014 |
| WO | 2015/085138 A1 | 6/2015 |
| WO | WO-2015132668 A1 | 9/2015 |
| WO | 2016/028591 A1 | 2/2016 |
| WO | 2016/044223 A1 | 3/2016 |
| WO | 2016/183495 A2 | 11/2016 |

OTHER PUBLICATIONS

European Search Report from EP17166472.5, dated Nov. 7, 2017, 7 pages.

International Preliminary Report on Patentability for PCT/US2012/055537, dated Mar. 18, 2014, 10 pages.

International Preliminary Report on Patentability for PCT/US2012055445 dated Mar. 18, 2014, 9 pages.

International Search Report & Written Opinion in International Application No. PCT/US/2012/055445, dated Dec. 5, 2012, 15 pages.

International Search Report and Written Opinion for PCT/US2012/055537, dated Dec. 5, 2012, 5 pages.

International Search Report and Written Opinion for PCT/US2012/061928 dated Jan. 22, 2013, corresponding to U.S. Appl. No. 13/658,597, 8 pages.

International Search Report and Written Opinion for PCT/US2013/022404 dated May 8, 2013, corresponding to U.S. Appl. No. 13/743,118, 7 pages.

International Search Report and Written Opinion for PCT/US2014/066153 dated Feb. 17, 2015, corresponding to U.S. Appl. No. 14/084,592, 5 pages.

International Search Report and Written Opinion from PCT/US2016/032487, dated Dec. 14, 2016, 20 pages.

Search Report and Written Opinion from PCT/US2018/056031, dated February 1, 2019, 18.

Ueda et al, Incomplete Endograft Apposition to the Aortic Arch: Bird-Beak Configuration Increases Risk of Endoleak Formation after Thoracic Endovascular Aortic Repair, Radiology: vol. 255 No. 2; May 2010, pp. 645-652.

International Preliminary Reporton Patentability for PCT Patent Application No. PCT/US2016/032487, dated Nov. 23, 2017, 13 pages.

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

International Preliminary Reporton Patentability for PCT Patent Application No. PCT/US2018/056031, dated Apr. 30, 2020, 11 pages.

* cited by examiner

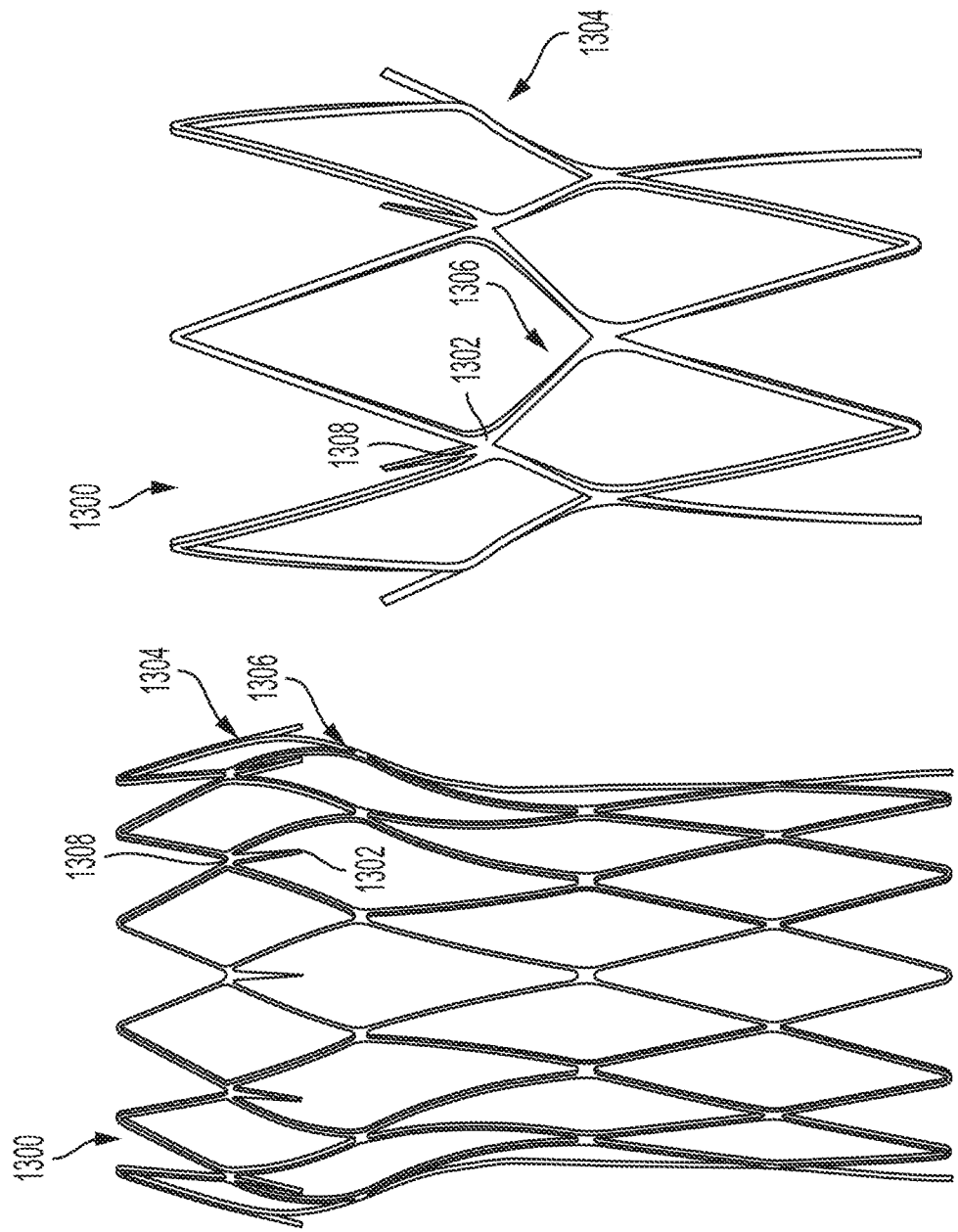

MEDICAL DEVICES AND ANCHORS THEREFOR

CROSS-REFERENCE TO RELATED APPLICATION

This application claims the benefit of Provisional Application No. 62/572,763, filed Oct. 16, 2017, which is incorporated herein by reference in its entirety for all purposes.

TECHNICAL FIELD

The present disclosure relates to implantable medical devices with movable fixation that may be used to occlude, filter and/or support apertures, conduits, spaces, organs, and other structures and/or openings within a patient.

BACKGROUND

Various medical devices require some form of fixation or anchoring to a targeted site. Common anchoring includes barbs, hooks, sutures or other features used to attach a device to the surrounding anatomy. Some examples of devices requiring fixation include vascular occluders/plugs, vascular filters, occluders, vena-cava filters, stents, stent grafts, bile/ urinary duct stents, gastrointestinal stents and liners, various monitors or diagnostic devices, central venous catheters, and other devices. For transcatheter delivery, these devices can be pre-loaded and constrained to a small profile to allow minimally invasive delivery to a site. Once positioned at the desired site, the constraining element is removed, allowing the device to self expand, or be balloon expanded, and engage the surrounding anatomy.

Current anchors often interfere with the device loading, reloading, or compaction process. For example, as the device is loaded into a small diameter constraining element, for example a catheter, the anchor can snag or puncture the constraining catheter. Anchors need sufficient engagement with the tissue typically by protrusion away from the implantable medical device body. This presents challenges when loading the device into a catheter because the anchors catch on the distal tip of the catheter, and the inside of the catheter, causing high loading forces, device damage, or catheter damage.

SUMMARY

Various aspects of the present disclosure provide implantable medical devices that may be used to occlude, filter and/or support apertures, conduits, space, organs and other structures or openings within a patient, including structures within the heart. This disclosure provides medical devices that can be deployed using transcatheter techniques (although various deployment techniques are contemplated) into a patient with anchors that retract and deploy in response to catheter loading and deployment, respectively. Various embodiments of the present disclosure are directed toward anchors that are displaced towards the central axis of the catheter during catheter loading the device into the catheter or reloading the device back into the catheter after deployment. The anchor tips displace sufficiently to eliminate contact/interaction with the catheter on loading. This is accomplished by utilizing a device body design, waist, and placement of the anchor base distal to the waist.

For illustration purposes, medical devices for occlusion of an atrial appendage of the patient will be described. The heart has left and right atrial appendages. Fixation is necessary to avoid embolization of the devices and in view of the dynamic movement of the heart as it beats.

According to one example, ("Example 1"), a device for placement in vessels, appendages, and openings in a body including a frame having a proximal end, a distal end, and a longitudinal axis, the device including: a first body portion; a waist portion angled relative to the longitudinal axis; and one or more anchors arranged along the waist portion and configured to rotate relative to and toward the longitudinal axis in response to the frame being arranged in a delivery configuration to avoid contact between an anchor tip and a delivery sheath.

According to another example, ("Example 2") further to Example 1, the device further includes a second body portion tapering inwardly relative to the longitudinal axis toward the distal end, and wherein the waist portion is arranged between the first body portion and the second body portion, and each of the one or more anchors include a root arranged at the waist portion, and the one or more anchors are configured to rotate toward the longitudinal axis at the root in response to the frame being arranged in the delivery configuration.

According to another example, ("Example 3") further to Example 2, the first body portion or the second body portion includes circumferentially extending row of strut pairs with adjacent strut pairs joining together, each of the one or more anchors include a tip at a distal end, and the one or more anchors are configured to move inwardly and arrange the tip between the adjacent strut pairs in response to the frame being arranged in the delivery configuration.

According to another example, ("Example 4") further to any one of Examples 2-3, the root includes a curvature with an angle between approximately −10 degrees to zero degrees, relative to the longitudinal axis, in the delivery configuration and an angle between approximately 10 degrees to 55 degrees, relative to the longitudinal axis, in the deployed configuration.

According to another example, ("Example 5") further to any one of Examples 1-4, the one or more anchors are configured to rotate toward the longitudinal axis at the waist portion in response to the frame being arranged in the delivery configuration.

According to another example, ("Example 6") further to Example 5, the waist portion includes a body angle relative to the first body portion and the second body portion, and the body angle facilitates rotation of the one or more anchors in response to the frame being arranged in the delivery configuration.

According to another example, ("Example 7") further to Example 6, the body angle is less than 180° in the deployed configuration.

According to another example, ("Example 8") further to Example 7, the one or more anchors include a radius in the deployed configuration that is less than or equal to the body angle According to another example, ("Example 9") further to any one of Examples 1-8, further comprising a second body portion and wherein a flexibility of the second body portion is less than a flexibility of the waist portion.

According to yet another example, ("Example 10"), a device for placement in vessels, appendages, and openings in a body having a delivery configuration and a deployed configuration, the device includes: a frame having a proximal end, a distal end, and a longitudinal axis, the frame including: a first body portion including a plurality of cells, a second body portion, a waist portion arranged between the first body portion and the second body portion and forming an angle of approximately between 20 degrees and 90 degrees between the first body portion and the second body portion, and at least one anchor having a root arranged at a distal end of the waist portion and a tip extending toward the proximal end, the at least one anchor projects outwardly relative to the longitudinal axis from the waist portion in the deployed configuration and nested within one or more of the plurality of cells in the delivery configuration.

According to another example, ("Example 11") further to Example 10, the at least one anchor is configured to rotate toward the longitudinal axis in response to the frame being arranged in the delivery configuration from the deployed configuration.

According to another example, ("Example 12") further to any one of Examples 10-11, the at least one anchor is configured to rotate relative to the longitudinal axis and move inwardly an anchor tip in response to the frame being arranged in the deployed configuration from the delivery configuration.

According to another example, ("Example 13") further to any one of Examples 10-12, the root of each of the at least one anchor is approximately 40% of a total device length from the distal end of the frame.

According to another example, ("Example 14") further to any one of Examples 10-13, at least one of a flexibility of the first body portion and a flexibility of the second body portion is less than a flexibility of the waist portion.

According to another example, ("Example 15") further to any one of Examples 10-14, widths of the adjacent strut pairs are reduced adjacent to the at least one anchor.

According to yet another example, ("Example 16"), a system for deployment of a device in vessels, appendages, and openings in a body, the system including: a delivery catheter having a lumen and substantially circular body portion; and a frame having a proximal end, a distal end, and a longitudinal axis, the frame including: a first body portion; a second body portion tapering inwardly relative to the longitudinal axis toward the distal end; a waist portion arranged between the first body portion and the second body portion; and one or more anchors arranged along the waist portion and configured to move inwardly relative to and toward the longitudinal axis in response to the frame being arranged within the delivery catheter to avoid contact between an anchor tip and the delivery catheter.

According to another example, ("Example 17") further to Example 16, the one or more anchors are configured to rotate toward the longitudinal axis without contacting the substantially circular body portion in response to being arranged within the delivery catheter.

According to another example, ("Example 18") further to any one of Examples 16-17, the one or more anchors are configured to move outwardly relative to the longitudinal axis in response to deploying the frame from the delivery catheter.

According to another example, ("Example 19") further to any one of Examples 16-18, the delivery catheter is configured to deploy the distal end of the frame prior to the proximal end of the frame, and the one or more anchors project outwardly from the waist portion and curve upward toward the proximal end in response to deploying the frame from the delivery catheter in a deployed configuration.

According to another example, ("Example 20") further to any one of Examples 16-19, the delivery catheter is configured to recapture the frame from the deployed configuration and rotate the one or more anchors toward the longitudinal axis in response to drawing the frame into the delivery catheter.

According to another example, ("Example 21"), a method for deploying a device in vessels, appendages, and openings in a body, the method including: arranging an implantable medical device for delivery, the implantable medical device having a first body portion, a second body portion tapering inwardly relative to the longitudinal axis toward the distal end, a waist portion arranged between the first body portion and the second body portion, and one or more anchors arranged along the waist portion; collapsing the device by loading device into a delivery catheter whereby the one or more anchors move inwardly toward the longitudinal axis in response to the frame being arranged within the delivery catheter; and implanting the device within the body by deploying the device from the delivery catheter and expanding the frame to a deployed configuration with the one or more anchors being configured to move radially outward from the longitudinal axis and engage tissue in the body.

According to another example, ("Example 22") further to Example 21, the method also includes reloading the device into the delivery catheter, after implanting the device, to disengage the one or more anchors from the tissue and rotate the one or more anchors toward the longitudinal axis.

According to another example, ("Example 23") further to Example 22, the method also includes re-implanting the device within the body, after reloading the device into the delivery catheter, with the one or more anchors being configured to rotate radially outward from the longitudinal axis and engage tissue in the body.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 13A shows an example frame for an implantable medical device with anchors in a proximal-facing arrangement, in accordance with various aspects of the disclosure.

FIG. 13B shows the example frame for an implantable medical device, shown in FIG. 13A, with anchors in a distal-facing arrangement, in accordance with various aspects of the disclosure.

Figure 1B:
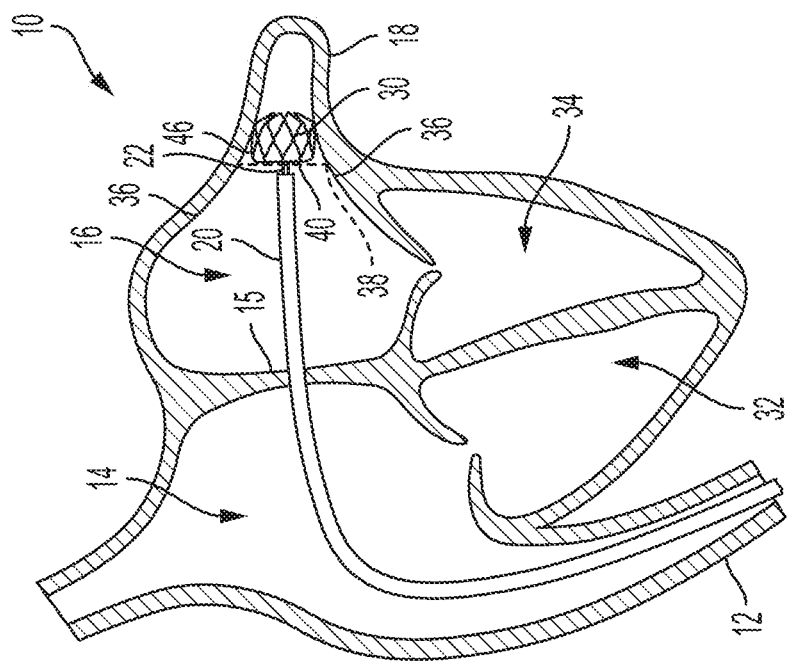
FIG. 1B shows the configuration of FIG. 1A with the implantable medical device deployed from the catheter delivery system and positioned within the LAA, in accordance with various aspects of the disclosure.

While the disclosure is amenable to various modifications and alternative forms, specific embodiments have been shown by way of example in the drawings and are described in detail below. The intention, however, is not to limit the disclosure to the embodiments described. On the contrary, the disclosure is intended to cover all modifications, equivalents, and alternatives falling within the scope of the disclosure as defined by the appended claims.

DETAILED DESCRIPTION

Various aspects of the present disclosure are directed to implantable medical device with anchors. The anchors may be configured to avoid damaging of a delivery catheter during loading into the delivery catheter and deployment from the delivery catheter in a patient. The medical devices have anchors that move radially relative to the longitudinal axis of the medical device when constrained for loading and when unconstrained for unloading from a constraining element, such as a catheter. In certain embodiments, the anchors may displace, retract, rotate, and/or fold toward or away from a longitudinal axis of the implantable medical device embodiment or outer perimeter of the implantable medical device. The anchors are configured to engage with the tissue (e.g., by protrusion away from the body of the implantable medical device) during or after deployment. Consistent with the deployment/engagement of the anchors in this manner, a portion of the anchors (e.g., anchor tips) avoid catching on a tip of the delivery catheter or the inside of the catheter which would cause high loading forces, device damage, or catheter damage. The anchors avoid contact/interaction with the delivery catheter. Some embodiments have anchors that are displaced away from the catheter during catheter loading. The anchor tips displace sufficiently to eliminate contact/interaction with the catheter on loading. This is accomplished by utilizing a device body design, waist, and placement of the anchor bases distal to the waist.

The implantable medical devices may be occlusive devices. The occlusive devices discussed herein are more capable of being recaptured and reloaded into a delivery catheter without causing damage to the surrounding tissue. For example, in some embodiments the anchor members of the occlusive devices are more capable of deflection during recapture and reloading. Additionally, in certain embodiments, the anchor members allow the occlusion device to fully reload into the delivery system without damage to the occlusion device and delivery system. Consequently, various embodiments of the occlusive devices provided herein may be removed from tissue essentially atraumatically. While the anchors of the occlusive devices provided herein are capable of atraumatic deflection during recapture and reloading, the anchors provide stable in vivo positioning.

In addition, it can be observed that certain embodiments of the occlusive devices provided herein are more conformable (less stiff) than the commercially available occlusive devices. Such enhanced conformability can provide better sealing (more consistent contact between the occlusive device and surrounding tissue), improved fatigue resistance, less trauma to the patient, and more stable positioning, to provide some example benefits. It can also be said that the embodiments of the occlusive devices provided herein are not designed to "drive" tissue into conformance with the occlusive devices. Rather, the occlusive devices are generally intended to conform themselves to the native topography of the surrounding tissue.

Figure 1C:
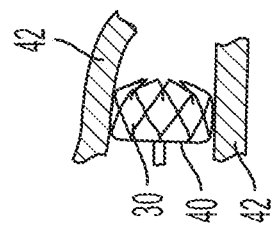
FIG. 1C shows the configuration of FIG. 1A with the implantable medical device deployed from the delivery system and positioned within a vessel, in accordance with various aspects of the present disclosure.
Figure 1A:
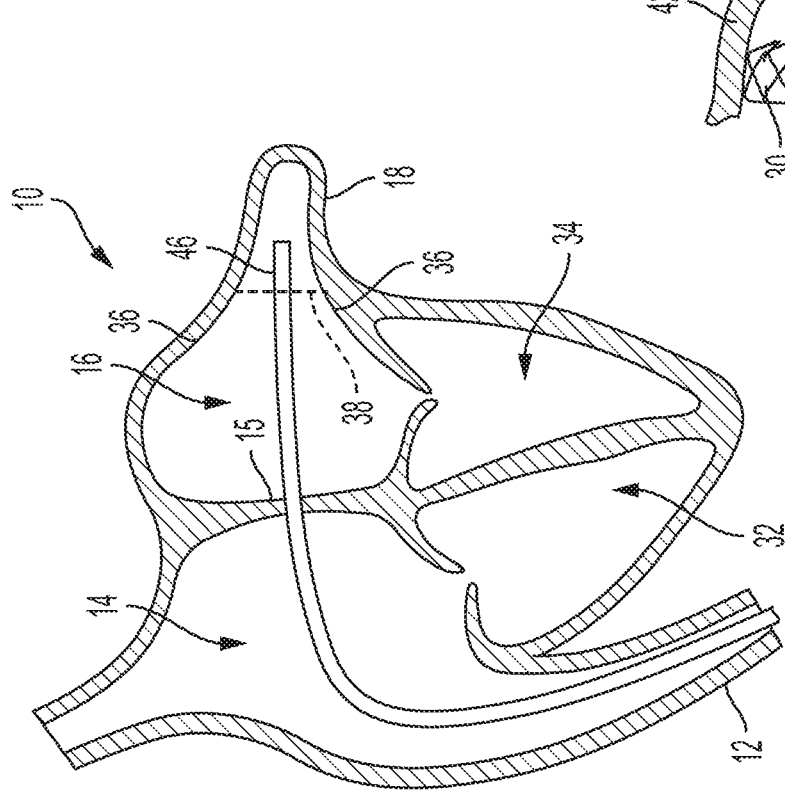
FIG. 1A is a cross-sectional view of a human heart in which a catheter delivery system is positioned in preparation for deployment of an implantable medical device into a left atrial appendage ("LAA") of the heart, in accordance with various aspects of the present disclosure.

FIGS. 1A-B are a cross-sectional views of a human heart 10 in which a delivery system 20 is positioned in preparation for deployment of an implantable medical device 30 into an appendage 18 of the heart, in accordance with various aspects of the present disclosure. FIGS. 1A-B show a depiction of a right atrium 14, a left atrium 16, a right ventricle 32, and a left ventricle 34 of the heart 10. As is shown, the appendage 18 is located in the left atrium 16 of the heart 10, and thus, the appendage 18 may be considered the left atrial appendage 18. Although the following discussion focuses on deployment of the implantable medical device 30 into the left atrial appendage 18, the implantable medical device 30 may be deployed in other appendages or openings within the human heart 10 or in other locations of the human body.

The left atrial appendage 18 may be considered a muscular pouch extending from the anterolateral wall 36 of the left atrium 16 of the heart 10, which serves as a reservoir for the left atrium 16. In a normal cardiac cycle, the left atrial appendage 18 may contract rhythmically with the rest of the left atrium 16 during contraction of the heart 10. Thus, during a normal cardiac cycle, the left atrial appendage 18 contracts with the left atrium 16 and pumps blood that may gather or collect within the left atrial appendage 18 to circulate therefrom. However, during cardiac cycles characterized by arrhythmias (e.g., atrial fibrillation), the left atrial appendage 18 may fail to sufficiently contract along with the left atrium 16, which can allow blood to stagnate within the left atrial appendage 18. Stagnant blood within the atrial appendage 18 is susceptible to coagulating and forming a thrombus, which can dislodge from the atrial appendage 18 and ultimately result in an embolic stroke. The implantable medical device 30, consistent with various aspects of the present disclosure, may be delivered to the left atrial appendage 18 to help prevent and militate against blood stagnation within the left atrial appendage 18.

In certain embodiments and as is shown in FIGS. 1A-B, the implantable medical device 30 may be delivered to the left atrial appendage 18 by way of a minimally invasive transcatheter procedure. More specifically, the delivery system 20 may be navigated through a vena cava 12, into the right atrium 14, through an atrial septum 15, and into the left atrium 16 towards the appendage 18. In some implementations, the percutaneous access to the patient's vasculature can be at the patient's femoral vein, for example. It should be understood that this example technique is merely one example, and many other access techniques can also be performed to deploy the occlusive devices provided herein. At this point of the deployment process, the occlusive device is contained within a lumen of the delivery system 20, and is configured in a collapsed low-profile delivery configuration. Although transcatheter systems are generally shown and described, other delivery systems (e.g., thoracoscopic) are also contemplated.

FIG. 1B shows the configuration of FIG. 1A with the implantable medical device 30 deployed from the delivery system 20 and positioned within the left atrial appendage 18, in accordance with various aspects of the present disclosure. As shown, a control catheter 22 may releasably couple to the implantable medical device 30, and is slidably disposed within the lumen of the delivery system 20. The control catheter 22 can be used by a clinician operator to make the implantable medical device 30 deploy from the delivery system 20. For example, after positioning the implantable medical device 30 through an ostium 38 of the left atrial appendage 18, the clinician operator can retract the delivery system 20 in relation to the control catheter 22 to unsheath and deploy the implantable medical device 30. The ostium 38 may be considered a portion of the anterolateral wall 36 of the left atrium 16 from which a taper originates to form the pouch-like structure of the left atrial appendage 18. The implantable medical device 30 may include an occlusive face 40 that is arranged near the ostium 38 of the left atrial appendage 18. The control catheter 22 may releasably couple to the implantable medical device 30 via a hub or center frame portion or a plug (or the like) inserted into the center frame portion arranged centrally within the occlusive face 40 of the implantable medical device 30.

After emerging from the constraining confines of the delivery system 20, the implantable medical device 30 can reconfigure to an expanded configuration. The implantable medical device 30 may expand to conform to the contours of the space defined within the left atrial appendage 18. In certain embodiments, positioning of the implantable medical device 30 relative to the ostium 38 of the left atrial appendage 18 may be enhanced and ensures that the implantable medical device 30 prevents thrombus from embolizing from the left atrial appendage 18. More specifically, the occlusive face 40 may be arranged within the left atrial appendage 18 such that the occlusive face 40 connects portions of the anterolateral wall 36 on opposite sides of the ostium 38 to form a substantially uniform surface. In certain instances, blood may collect or stagnate along the face of a device implanted therein if the occlusive face is non-uniform (e.g., a device having a hub that protrudes beyond other portions of the occlusive face; a device having an occlusive face that is concave, partially concave, or includes depressions, or a device having an occlusive face that is concave, partially concave) relative to the ostium 38 of the left atrial appendage 18 or the occlusive face includes protuberances. In these instances, thrombus may occur along the face of the implantable medical device 30 as a non-uniform surface may alter/disrupt the blood flow within the left atrium 18. Thus, a patient may remain susceptible to blood coagulation and thrombus formation if an implantable medical device 30 includes a non-uniform surface as the result of improper positioning or the design of the device.

After proper positioning and delivery of the implantable medical device 30, the control catheter 22 can be decoupled from the implantable medical device 30, and the delivery system 20 and control catheter 22 can be removed from the patient. With the implantable medical device 30 deployed as shown, the space defined within the left atrial appendage 18 is essentially separated from the left atrium 16 by virtue of the physical barrier provided by the implantable medical device 30. In this manner, stagnant blood within the LAA 18 that is susceptible to coagulating and forming thrombi may be prevented from entering the left atrium 16, and thereby prevented from potentially causing an embolic stroke. In addition, positioning of the occlusive face 40 of the implantable medical device 30 relative to the ostium 38 of the left atrial appendage 18 may help prevent blood collecting or stagnating along the face of the implantable medical device 30.

As noted above, the devices provided herein can be used in many different areas of the body, and that deployment of the implantable medical device 30 into the left atrial appendage 18 is merely one example implementation. More specifically, FIG. 1C shows the configuration of FIG. 1A with the implantable medical device 30 deployed from the delivery system and positioned within a vessel between the vessel walls 42, in accordance with various aspects of the present disclosure. At each implant location, forces (such as blood pumping or muscles contracting) acting on the implantable medical device 30 may threaten to dislodge the implantable medical device 30 from the implant location. As discussed in further detail below, the implantable medical device 30 may include anchors that may displace, retract, rotate, and/or fold toward the implantable medical device 30 and avoid catching on a tip or inside of the delivery system 20 and/or control catheter 22 which would cause high loading forces, device damage, or catheter damage.

Figure 2:
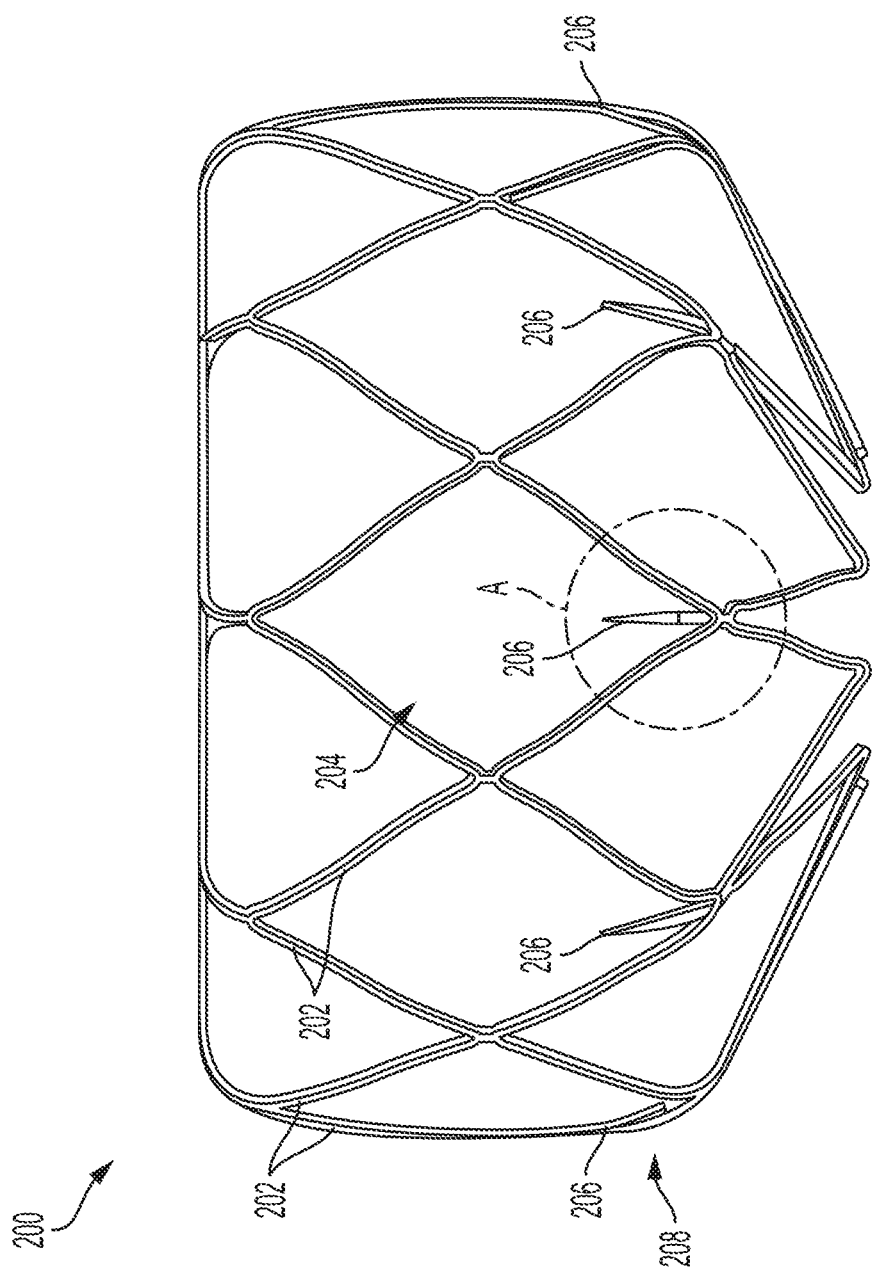
FIG. 2 shows an example frame for an implantable medical device, in accordance with various aspects of the disclosure.

FIG. 2 shows an example frame 200 for an implantable medical device, in accordance with various aspects of the present disclosure. The implantable medical device may be a device for placement in vessels, appendages, and openings in a body. The frame 200 may be a unitary frame formed of a plurality of struts 202 (FIG. 2 highlights four of the plurality of struts 202 for ease of understanding). In certain embodiments, the frame 200 may be unitary and self-expanding. The frame 200 may include body portions that have different shapes, angles, or other features (as explained in further detail with reference to FIG. 4) or may be another shape such as cylindrical, conical, frustoconical, hemispherical, a spherical cap, pyramidal, truncated pyramidal, and the like, and combinations thereof. Any and all combinations and sub-combinations of such varying shapes and varying geometries of shapes are envisioned and within the scope of this disclosure.

The frame 200 may include any number of rows and cells formed by the struts 202. The struts 202 may form multiple cells in a row. A single cell 204 is highlighted (as shown, the frame 200 includes multiple similar cells). The cell(s) 204 may be formed of a five-sided shape, a six-sided shape, or other shapes such as, but not limited to, polygonal, square, rectangular, parallelogram-shaped, rhomboidal, trapezoidal, diamond-shaped, chevron-shaped, octagonal, triangular, and the like. As shown in FIG. 2, the frame 200 tapers inwardly at distal portion of the cell 204. The point at which the frame 200 transitions to the taper is a waist portion 208 of the frame 200.

In addition to transitioning the frame 200 to a tapered portion, one or more anchors 206 may also be located at the waist portion 208. The one or more anchors 206 may be located at a portion of the cell 204 near or at which struts 202 converge. The one or more anchors 206, arranged along the waist portion 208 configured to move inwardly (e.g., rotate) relative to and toward the longitudinal axis in response to the frame 200 being arranged in a delivery configuration. The one or more anchors 206 may retract, move or rotate inwardly such that when the frame 200 is loaded into a delivery catheter and into the delivery configuration (e.g., collapsed for transcatheter delivery), the one or more anchors 206 are not caught on the delivery catheter during loading of the frame 200 therein. In certain instances, the anchors 206 rotate to avoid contact between an anchor tip and a delivery catheter. The waist portion 208, in certain embodiments, facilitates the one or more anchors rotating by acting as a hinge of the frame 200. The frame 200 collapses inwardly when being arranged in the delivery configuration, and the waist portion 208 may facilitate rotating of the one or more anchors 206. The anchor 206 is arranged within a portion of the frame 200 about a circumference of the frame 200 and within each of the cell(s) 204 that together form a circumferentially extend row of pairs of struts 202. As shown in FIG. 2, an area of the frame 200 is highlighted ("A"), which is shown in further detail in FIGS. 3A-C.

Figure 3A:
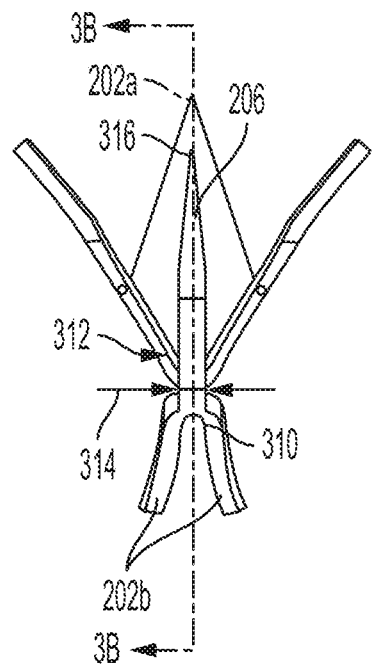
FIG. 3A is a front view of an anchor of an implantable medical device, in accordance with various aspects of the disclosure.

FIG. 3A is a front view of an anchor 206 of an implantable medical device, in accordance with various aspects of the present disclosure. As shown in FIG. 3A, adjacent pairs of struts 202a converge together, within the cell(s) 204, at a junction 310. More specifically, the struts 202a join together, and the struts 202b continue and split apart at the waist portion 208. The junction 310 is present in each of the cell(s) 204, shown in FIG. 2, as formed by the struts 202b joining together. Although FIG. 2 shows multiple junctions 310, the implantable medical device, consistent with various aspects of the present disclosure, may include any number (one, two, three, four, five, six, twelve, twenty-four, or any number therebetween) cell(s) 204.

The anchors 206 may be arranged at or adjacent to the junction 310. As shown in FIG. 3A, the anchors 206 extend from the junction 310. More specifically, the anchors 206 include an anchor root 312 that is located at (as shown in FIG. 3A) or adjacent to the junction 310. In certain embodiments the anchor root 312 is approximately 25% to 60% of the total frame 200 length as measured from the distal end of the frame 200. The anchors 206 extend between the struts 202a, and may be configured to move inwardly (e.g., rotate) toward a longitudinal axis of the frame 200 (e.g., by pivoting) at the root 312 in response to the frame 200 being arranged in the delivery configuration. The anchors 206 may rotate and inward and therefore retract relative to the longitudinal axis of the frame 200. In certain instances, the anchors 206 rotate to avoid contact between an anchor tip 316 and a delivery catheter. In certain instances, tips 316 of the anchors 206 avoid contact with the delivery catheter or sheath. The anchors 206 rotating when transitioned to the delivery configuration brings the tips 316 (which may be approximately 1%, 2%, 3%, 4%, 5%, 6%, 7%, 8%, 9%, 10% of a length of the anchor 206 as measured from the distal end) away from an out of contact with the delivery catheter or sheath. In other instances, the anchors 206 rotating in this manner brings the tips 316 to the interior of the frame 200. In certain instances, the anchors 206 rotate and the anchor tips 316 move inwardly.

Figure 6A:
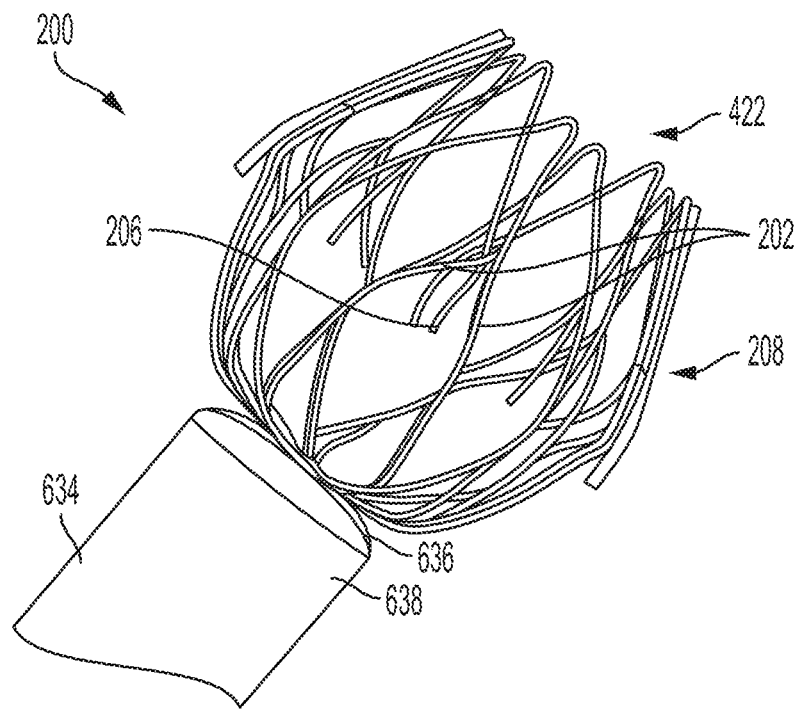
FIG. 6A shows an example frame and anchors with a delivery catheter in a first configuration, in accordance with various aspects of the disclosure.
Figure 6B:
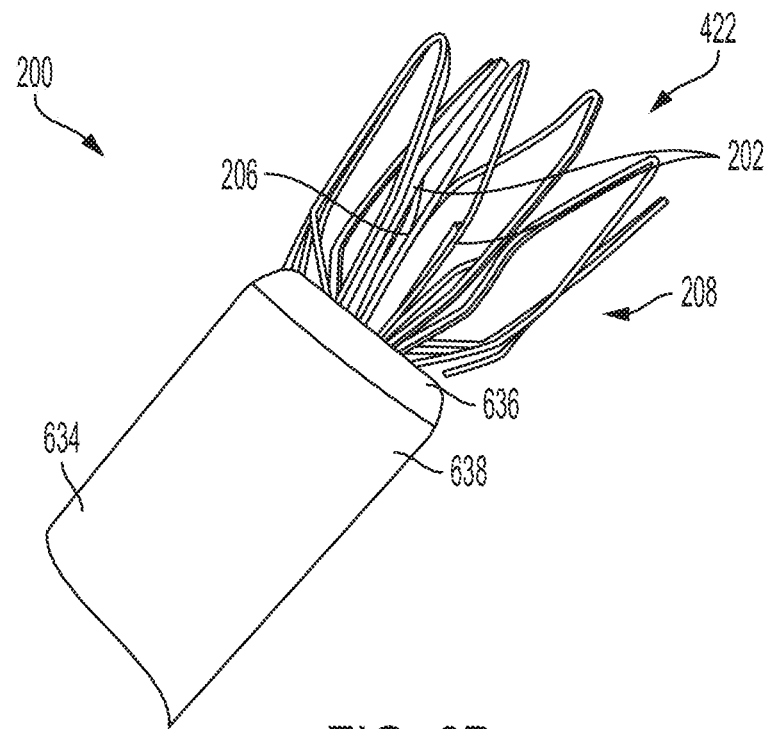
FIG. 6B shows the frame, anchors, and the delivery catheter, as shown in FIG. 6A, in a second configuration, in accordance with various aspects of the disclosure.

The root 312 is arranged at the waist portion 208 of the frame 200. As noted above, the waist portion 208 occurs at an angle change or taper of the frame 200. In collapsing the frame 200 to a delivery configuration (e.g., elongation of the device to fit within a delivery catheter as shown in FIGS. 6A-B), the angle change or taper of the frame 200 at the waist portion 208 facilitates movement (e.g., retracting/rotating) of the anchors 206 inwardly. Thus, the anchors 206 are configured to rotate toward the longitudinal axis at the waist portion 208 in response to the frame 200 being arranged in the delivery configuration.

Figure 3B:
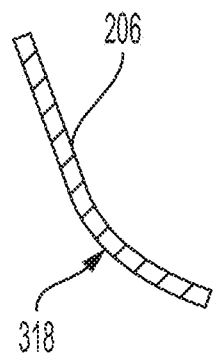
FIG. 3B is a side view of the anchor, as shown in FIG. 3A, in accordance with various aspects of the disclosure.

In certain embodiments, the anchors 206 taper from a base 314, arranged at the root 312, to the tip 316. Tapering from the base 314 to the tip 316 may facilitate the ability of the anchors 206 to puncture tissue. As viewed from the "B" line in FIG. 3A, FIG. 3B is a side view of the anchor, as shown in FIG. 3A, in accordance with various aspects of the present disclosure. As shown in the side view, the anchors 206 include a constant depth through a length thereof with the width of the anchors 206 tapering toward the tip 316. In addition and as shown in FIG. 3B, the anchors 206 include a curvature 318. The curvature 318, in the deployed configuration of the frame 200, extends the anchors 206 outwardly from the frame 200. The curvature 318 is remains constant when transitioning the frame 200 from the deployed configuration (shown in FIG. 2) to a delivery configuration while curvature of adjacent struts 202a is altered. In certain embodiments, the curvature 318 of the anchors 206 decreases such that the anchors 206 rotate inwardly relative to the frame 200 and between the struts 202a.

In certain embodiments, the curvature 318 of the root has an angle between approximately (plus or minus 1%) −10 degrees to zero degrees, relative to the longitudinal axis, in the delivery configuration and an angle between approximately (plus or minus 1%) 10 degrees to 55 degrees, relative to the longitudinal axis, in the deployed configuration as shown in FIG. 3B. In other instances, the curvature 318 of the root has an angle between approximately (plus or minus 1%) −30 degrees to 10 degrees, relative to the longitudinal axis, in the delivery configuration and an angle between approximately (plus or minus 1%) 5 degrees to 65 degrees, relative to the longitudinal axis, in the deployed configuration as shown in FIG. 3B. The curvature 318 of the anchor may be measured from a tangent through the tip 316 and the base 314. The curvature 318 may be between 5 to 90 degrees in certain instances. In certain instances, the tip 316 of the anchor 206 may protrude outwardly relative to the struts 312 by between approximately 0.2 mm and approximately 1 mm. As noted with reference to FIG. 6A and FIG. 6B, the tip 316 of the anchor 206 may rotate when transitioning from a deployed to a delivery configuration to avoid contacting a delivery sheath. The amount of anchor 206 protrusion may relate to a combination of the curvature 318 of the anchor and the length of the anchor 206. As a result and in certain instances, the combination of the curvature 318 of the anchor and the length of the anchor 206 results in an anchor 206 that extends outwardly from the struts 312 by between approximately 0.2 mm and approximately 0.7 mm or between approximately 0.4 mm and approximately 0.6 mm.

Figure 3C:
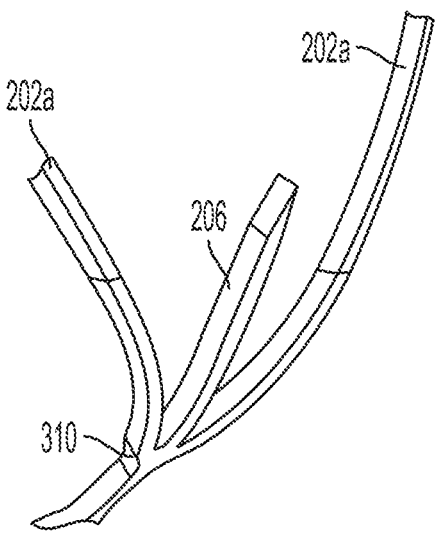
FIG. 3C is a perspective view of the anchor, as shown in FIGS. 3A-B, in accordance with various aspects of the disclosure.

FIG. 3C is a perspective view of the anchor 206, as shown in FIGS. 3A-B, in accordance with various aspects of the present disclosure. As shown in FIG. 3C, the anchors 206 extend outwardly relative to the struts 202a.

Figure 4:
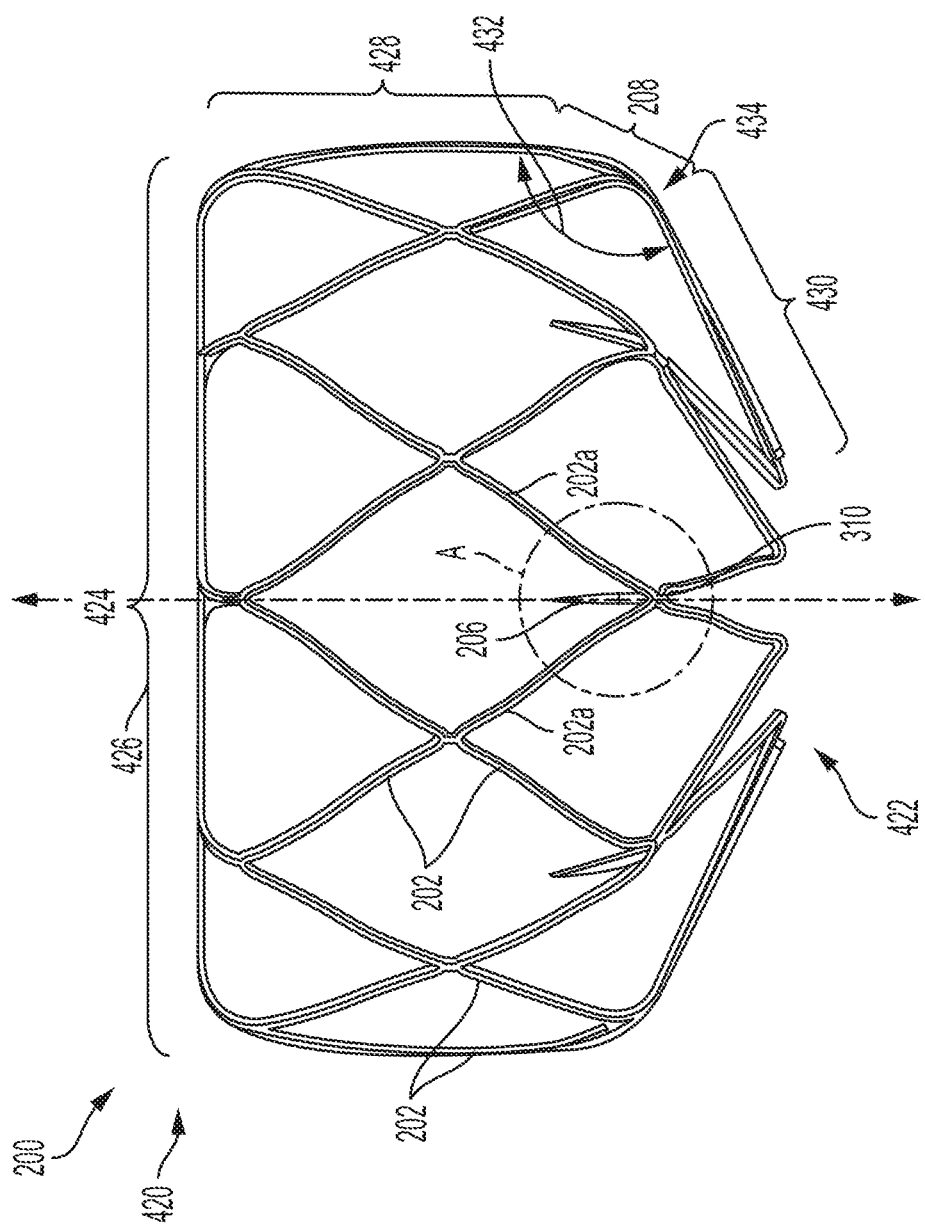
FIG. 4 shows another example frame for an implantable medical device, in accordance with various aspects of the disclosure.

FIG. 4 shows another example frame 200 for an implantable medical device, in accordance with various aspects of the present disclosure. The implantable medical device may be a device for placement in vessels, appendages, and openings in a body. The frame 200 may include a proximal end 420, a distal end 422, and a longitudinal axis 424. The frame 200 includes a face portion 426 at the proximal end 420 of the frame 200.

In addition, the frame 200 includes a first body portion 428 that includes a circumferentially extending row of strut pairs 202 with adjacent strut pairs 202a converging together at one or more junctions 310 of the frame. Although the frame includes multiple adjacent strut pairs 202a and junctions 310, a single set of the adjacent strut pairs 202a and a single one of the junctions 310 is highlighted in FIG. 4 for ease of understanding. The frame 200 also includes a second body portion 430 arranged distally of the first body portion 428. The second body portion 430 may taper inwardly relative to the longitudinal axis 424 toward the distal end 422. In addition, the frame 200 may include a waist portion 208 arranged between the first body portion 428 and the second body portion 430.

The frame 200 also includes anchors 206 (a single one of the anchors 206 is highlighted in FIG. 4 for ease of understanding). The anchors 206 are arranged along or within the waist portion 208 at or adjacent to the junctions 310. In addition, the anchors 206 are configured to move inwardly (e.g., rotate) relative to and toward the longitudinal axis 424 in response to the frame 200 being arranged in a delivery configuration (e.g., as shown in FIGS. 6A-B). In certain embodiments, the waist portion 208 may include a body angle 432 relative to the first body portion 428 and the second body portion 430. The body angle 432 may facilitate rotating of the anchors 206 in response to the frame 200 being arranged in the delivery configuration. As shown in FIG. 4, the anchors 206 are arranged at a distal end 434 of the waist 208. In certain embodiments, the root (e.g., as shown in FIGS. 3A-C) of the anchors 206 are at the distal end 422 of the waist 208.

In addition, the anchors 206 are configured to move outwardly from the longitudinal axis 424 in response to the frame 200 arranged in the deployed configuration from the delivery configuration. The anchors 206 being configured to move outwardly from the longitudinal axis 424 when deployed from a delivery catheter allows for the anchors 206 to be implanted within tissue of the body.

In the delivery configuration, the frame 200 is elongated and collapsed relative to the longitudinal axis 424. The waist portion 208 and body angle 432 of the waist portion 208, for example, acts as a hinge to facilitating rotating of the anchors 206 in response to the frame 200 being arranged in the delivery configuration. The waist portion 208 compresses inwardly prior to or at a faster rate than the remaining portions of frame 200, which carries the anchors 206 inwardly. In certain embodiments, the body angle 432 is less than 180° in the deployed configuration as shown in FIG. 4. In certain embodiments, the body angle 432 is between approximately (plus or minus 1%) 20 degrees and 90 degrees. In addition, the flexibility of the first body portion 428 and/or flexibility of the second body portion 430 may be less than the flexibility of the waist portion 208 to further facilitate the waist portion 208 functioning as a hinge to move the anchors 206 inwardly and outwardly. In certain instances, flexibility of the frame 200 or portions of the frame 200 may be a longitudinal bending flexibility. For example, the waist portion 208 may be more flexible than one or both of the first body portion 428 and the second body portion 430. The waist portion 208 may be softer than one or both of the first body portion 428 and the second body portion 430 in certain instances.

In certain embodiments, the frame 200 has a single change in angle, the body angle 432, may facilitate movement of the anchors 206 inwardly and outwardly. As noted above, the frame 200 collapses when arranged in the delivery configuration from the deployed configuration. During this transition, the body angle 432 straightens from the collapsing of the frame 200. The angle change for the frame at the body angle 432 allows the frame 200 to have a hinge point to retract the anchors 206 inwardly. The frame 200 not including multiple angle changes facilitates uniform collapsing of the frame 200 (e.g., as seen in FIGS. 6A-B) without forcing the frame 200 to fold inwardly at multiple inflection points, which may lead to uneven collapsing of a frame without retraction or rotation of anchors. Further, the frame 200 having an open distal end 422, as shown in FIG. 4, also facilitates retraction or rotating of the anchors 206. The distal end 422 being open (e.g., without a hub component) allows for the frame 200 to fold inwardly without a closed end inhibiting free movement of the distal end 422 to remain expanded or deployed and facilitating the frame 200 collapsing to an elongated delivery configuration. In this manner, the frame 200 collapses by retracting into a delivery catheter (e.g., as seen in FIGS. 6A-B) without the need for the application of a collapsing force to the distal end 422. The anchors 206 are also held inwardly without the delivery catheter holding or forcing the anchors 206 in a collapsed position. The rotating of the anchors 206 outwardly may occur without assistance of the delivery catheter.

The illustrative components shown in FIG. 4 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 4 may be, in embodiments, integrated with various other components depicted therein (and/or components not illustrated), all of which are considered to be within the ambit of the disclosed subject matter. For example, the frame 200 described with reference to FIG. 2 may be used in connection with a delivery system (shown in FIGS. 1A-B and FIGS. 6A-B). More specifically, the frame 200 may form a portion of implantable medical device 30. In addition, the frame 200 may include a membrane attached thereto (e.g., as shown and discussed with reference to FIG. 1).

Figure 5:
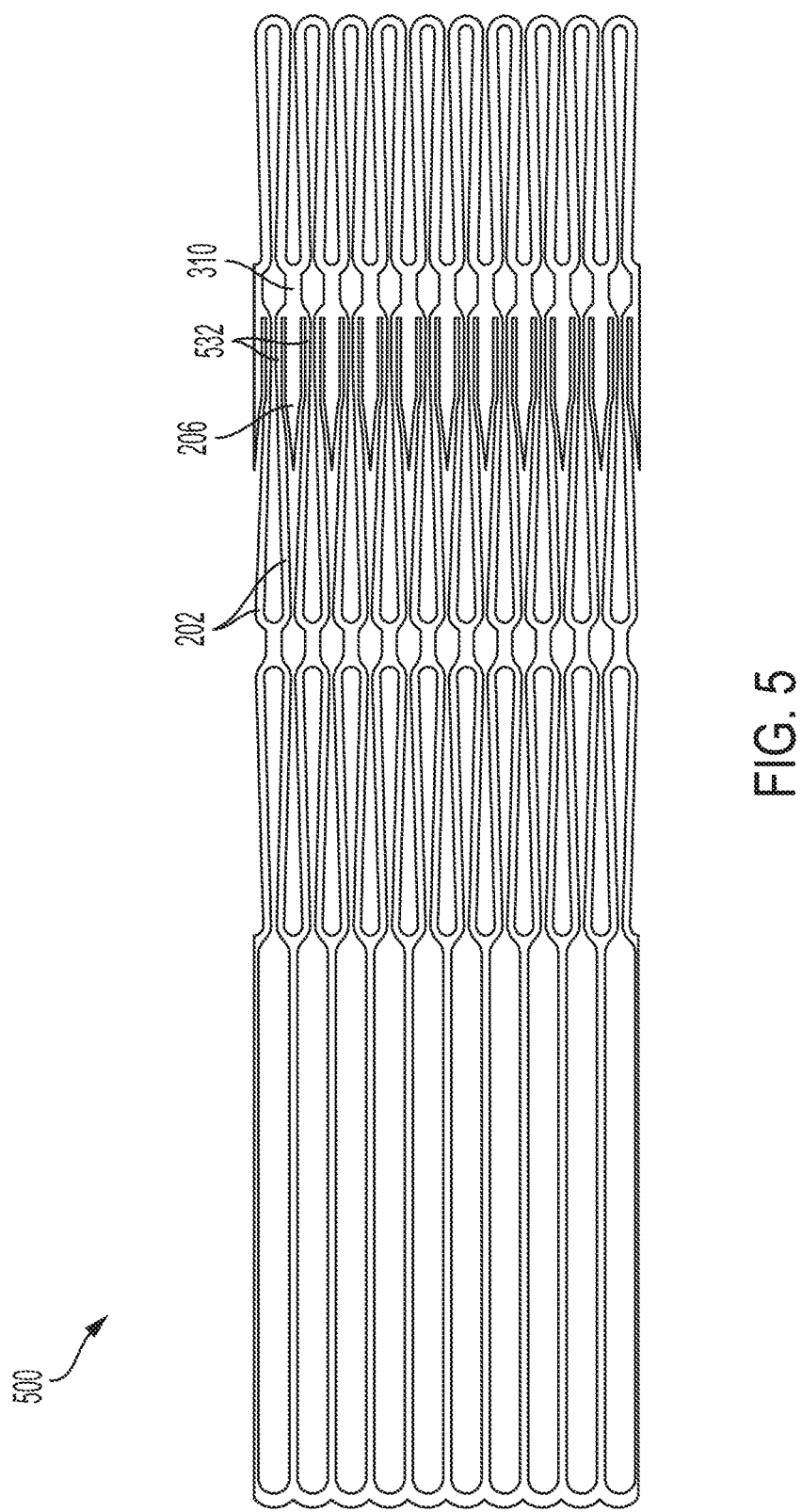
FIG. 5 is a side view of a strut cut pattern of a frame, prior to deformation to a shape set configuration, in accordance with various aspects of the disclosure.

FIG. 5 is a side view of a strut cut pattern 500 of a frame, prior to deformation to a shape set configuration (e.g., as shown in FIGS. 2 and 4), in accordance with various aspects of the present disclosure. A nitinol sheet material may be utilized. Pattern 500 results in the frame with anchors 206. The pattern 500 can also be used to form a plurality of struts 202.

As shown in FIG. 5, the struts 202 (a single adjacent pair is highlighted for ease of understanding) generally include a common width throughout the pattern 500. The struts 202, however, include a portion of reduced width 532 adjacent the anchors 206. The reduced width 532 portions are adjacent each anchor 206 widthwise, and adjacent each junction 310 lengthwise. In certain embodiments, the reduced width 532 portions may correspond to the waist portion 208 of the frame 200 (e.g., as shown in FIGS. 2 and 4). In certain embodiments, the reduced width 532 portions facilitate the waist portion 208 having a greater flexibility than other portions of the frame 200. In other embodiments, the waist portion 208 is heat treated different than other portions of the frame 200 (in addition to or alternatively from the reduced width 532 portions) to enhance flexibility.

500500500 FIG. 6A shows an example frame 200 and anchors 206 with a sheath 634 (or delivery device such as a delivery catheter) in a first configuration, in accordance with various aspects of the present disclosure. The first configuration shown in FIG. 6A may be considered a deployed configuration of the frame 200 (e.g., as shown in FIGS. 2 and 4). The anchors 206 project outwardly relative to the frame 200. The deployed configuration may be prior to the frame 200 being loaded into the sheath 634 for implantation in to the body, and also after the frame 200 is unloaded or deployed from the sheath 634 into the body.

FIG. 6B shows the frame 200, anchors 206, and the sheath 634, as shown in FIG. 6A, in a second configuration, in accordance with various aspects of the present disclosure. The second configuration shows the frame 200 being withdrawn into or deployed from the sheath 634. The frame 200 is not completely in a delivery configuration (e.g., within the sheath 634). As shown in comparing FIGS. 6A and 6B, the anchors 206, which had been projecting outwardly the deployed configuration shown in FIG. 6A, have moved inwardly (e.g., rotated) relative to and toward the longitudinal axis in response to the frame 200 being withdrawn into the sheath 634. The anchors 206, in certain embodiments, are substantially aligned with the adjacent struts 202 in the delivery configuration.

The sheath 634 includes a substantially circular body portion 636 at a distal end of the sheath 634. The substantially circular body portion 636 is an entry/exit point for a lumen 638 into which the frame 200 may be withdrawn for subsequent deployment or redeployment of the frame 200. As shown in FIG. 6B, the anchors 206, in response to the frame 200 being transitioned to the delivery configuration, the anchors 206 are configured to rotate inwardly such that the anchors 206 do not contact the substantially circular body portion 636 (or other portions of) the sheath 634. Portions of the anchors 206 (such as the anchor tips) also may avoid contact with the lumen 638 of the sheath 634 when withdrawn therein. In the absence of the anchors 206 being configured to rotate inwardly in this manner, a user operating the sheath 634 would encounter a large resistance when attempting to withdraw the frame 200 in the sheath 634. The anchors 206 being configured to rotate inwardly avoids unnecessary resistance in the deployment process. The unnecessary resistance could also damage the frame 200 itself by irreparably pleating or folding the frame 200. Thus, the anchors 206 being configured to rotate inwardly in this manner avoids damaging the sheath 634, avoids damaging the frame 200, and eases delivery and deployment of the implantable medical devices that include the frame 200. In certain instances, tips of the anchors 206 avoid contact with the sheath 634. The anchors 206 rotating when transitioned to the delivery configuration brings a tip (which may be approximately 1%, 2%, 3%, 4%, 5%, 6%, 7%, 8%, 9%, 10% of a length of the anchor 206 as measured from the distal end) away from an out of contact with the sheath 634. In other instances, the anchors 206 rotating in this manner brings the tip to the interior of the frame 200.

The anchors 206 are also configured to move outwardly from the longitudinal axis in response to deploying the frame 200 from the sheath 634. In addition to demonstrating the configuration or positioning changes of the anchors 206 when the frame transitions from the deployed configuration to the delivery configuration, the outward deflection of the anchors 206 is demonstrated in comparing the second configuration in FIG. 6B to the first configuration in FIG. 6A. As shown in FIG. 6B, the distal end 422 of the frame has expanded as it is retracted into the sheath 634. The open distal end 422 facilitates transmission of the collapsing force throughout the entirety of the frame to allow the frame 200 to collapse into an elongated delivery configuration. In this manner, the frame 200 collapses by retracting into the sheath 634 without the need for the application of a collapsing force to the distal end 422.

The sheath 634 is configured to deploy a distal end 422 of the frame prior 200 to the proximal end (shown contacting the substantially circular body portion 636 of the sheath 634 in FIG. 6A) of the frame 200. In addition, the anchors 206 project outwardly (from a waist portion 208) and curve upward toward the proximal end in the deployed configuration shown in FIG. 6A. The anchors 206 move outwardly in response to deploying the frame 200 from the sheath 634.

In certain embodiments, a user of the sheath 634 may recapture the frame 200 (and implantable medical device) within the sheath 634. After implanting the frame 200 within the body by deploying the frame 200 from the sheath 634 and expanding the frame 200 to the deployed configuration, placement of the frame 200 may not be in the intended location or at the intended angle. Thus, the user may wish to recapture and redeploy the frame 200. In these embodiments, the sheath 634 is configured to withdraw the frame 200 into the sheath 634 (into the delivery configuration) with the anchors 206 being configured to rotate radially inwardly and disengage from the tissue in the body. The anchors 206 atraumatically disengage from the tissue due to the retracting motion.

Figure 7:
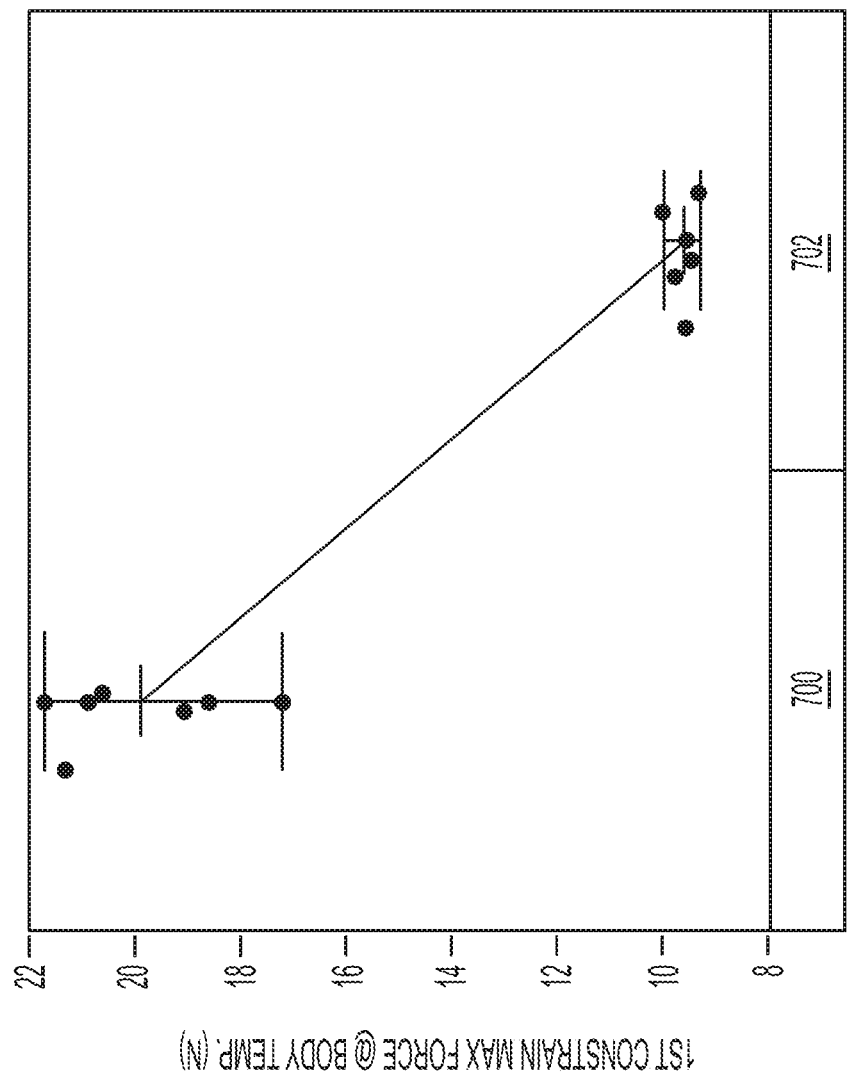
FIG. 7 shows a comparison of force for constraining an implantable device having a non-moveable or retractable anchor and the implantable device having a moveable or retractable anchor, in accordance with various aspects of the disclosure.

FIG. 7 shows a comparison of force for constraining an implantable device having a non-moveable or retractable anchor 700 and the implantable device having a moveable or retractable anchor 702, in accordance with various aspects of the present disclosure. FIG. 7 shows a plot of data indicating a range of measured forces for each of the non-moveable or retractable anchor 700 and the moveable or retractable anchor 702. The data simulates the force a user would encounter when attempting to withdraw an implantable medical device having the non-moveable or retractable anchor 700 or the moveable or retractable anchor 702 arranged with the implantable medical device.

As shown in FIG. 7, in order to constrain the non-moveable or non-retractable anchor 700, a larger or higher range of force is required as compared to the moveable or retractable anchor 702. The moveable or retractable anchor 702 enhances an implantable medical device's ability to constrain within a delivery configuration, as discussed in detail herein.

Figure 8:
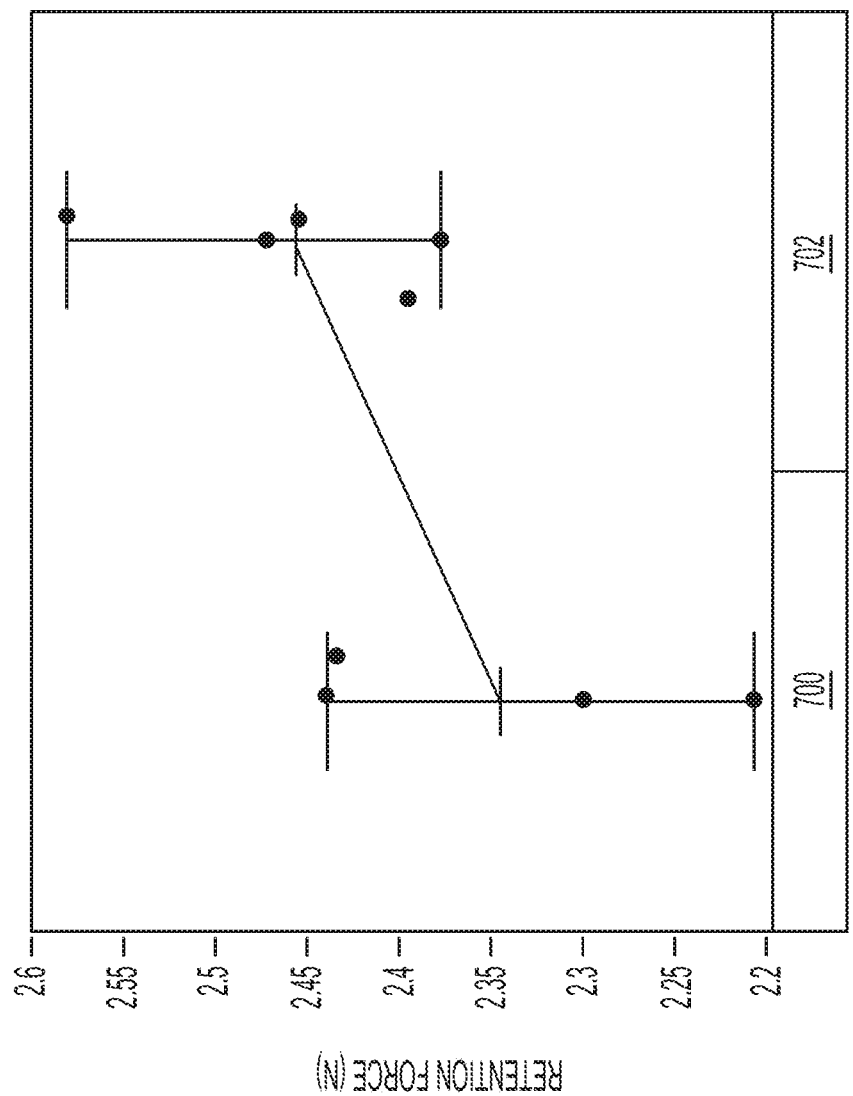
FIG. 8 shows a comparison of retention force of a non-moveable anchor and a retention force of a movable or retractable anchor, in accordance with various aspects of the disclosure.

FIG. 8 shows a comparison of retention force of a non-moveable or non-moveable anchor 700 and a moveable (e.g., rotatable) or retractable anchor 702, in accordance with various aspects of the present disclosure. FIG. 8 shows a plot of data indicating a range of measured retention forces that each of the non-moveable or non-retractable anchor 700 and the moveable or retractable anchor 702 are able to provide. The data simulates the retention force of the non-moveable or non-retractable anchor 700 or the moveable or retractable anchor 702 when arranged with an implantable medical device.

As shown in FIG. 8, the non-moveable or non-retractable anchor 700 has a lower range of retention force as compared to the moveable or retractable anchor 702. The moveable or retractable or rotatable anchor 702 enhances an implantable medical devices ability to retain the implantable medical devices at an implantation site, as discussed in detail herein.

Figure 9:
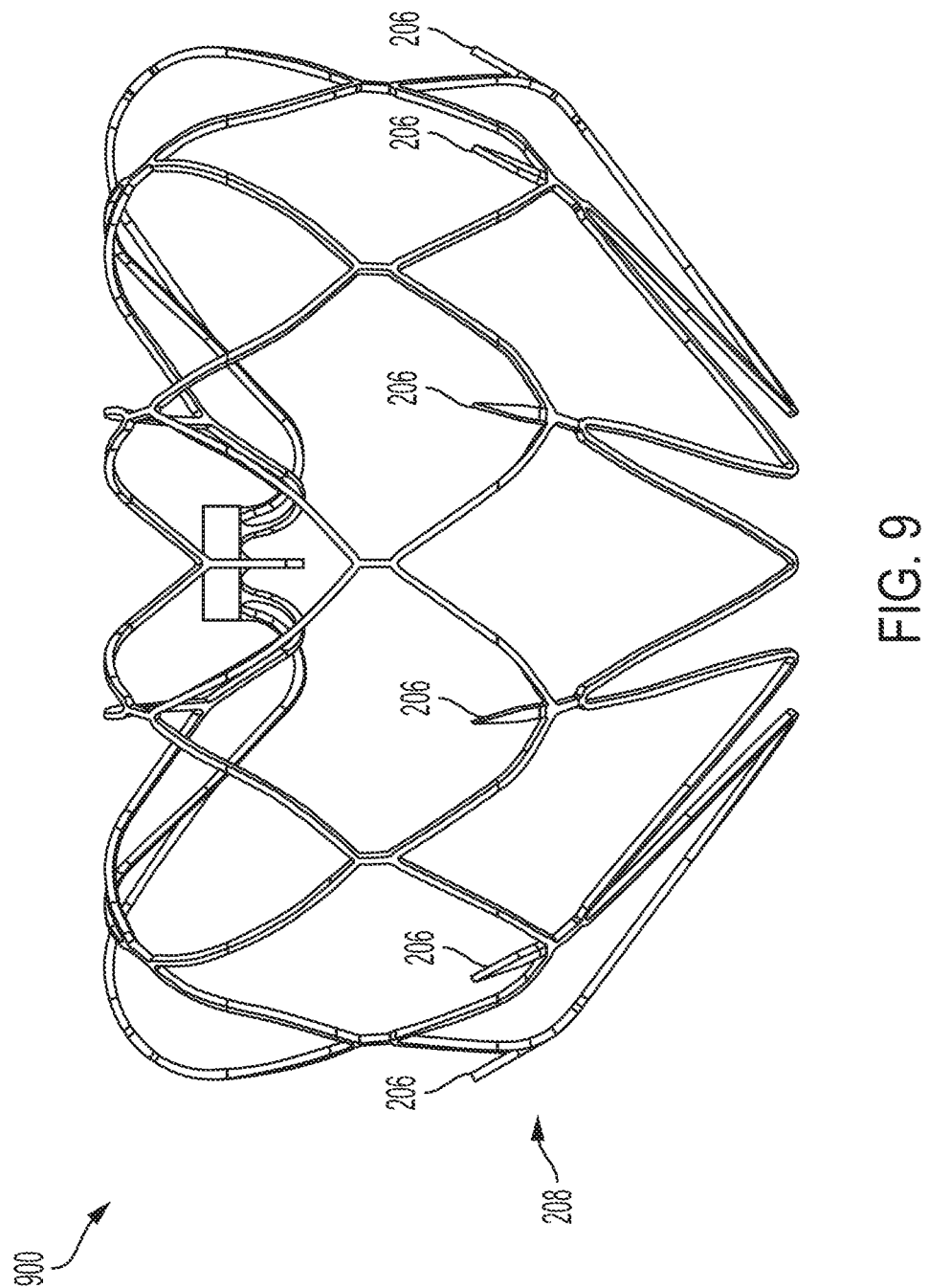
FIG. 9 shows another example frame for an implantable medical device, in accordance with various aspects of the disclosure.

FIG. 9 shows another example frame 900 for an implantable medical device, in accordance with various aspects of the present disclosure. As shown in FIG. 9, the frame 900 includes a different configuration than the frame 200 of FIG. 2 and the frame 200 of FIG. 4. Similar to the frame 200 of FIG. 2 and the frame 200 of FIG. 4, the frame 900 includes a waist portion 208 and anchors 206 arranged at the waist portion 208. The waist portion 208 is located on the frame 900 where the frame 900 beings to taper toward its distal end.

In addition, the anchors 206 are configured to rotate inwardly in response to the frame 900 being arranged in a delivery configuration. The waist portion 208 may act as a hinge to facilitate the anchors 206 being configured to rotate inwardly.

Figure 10:
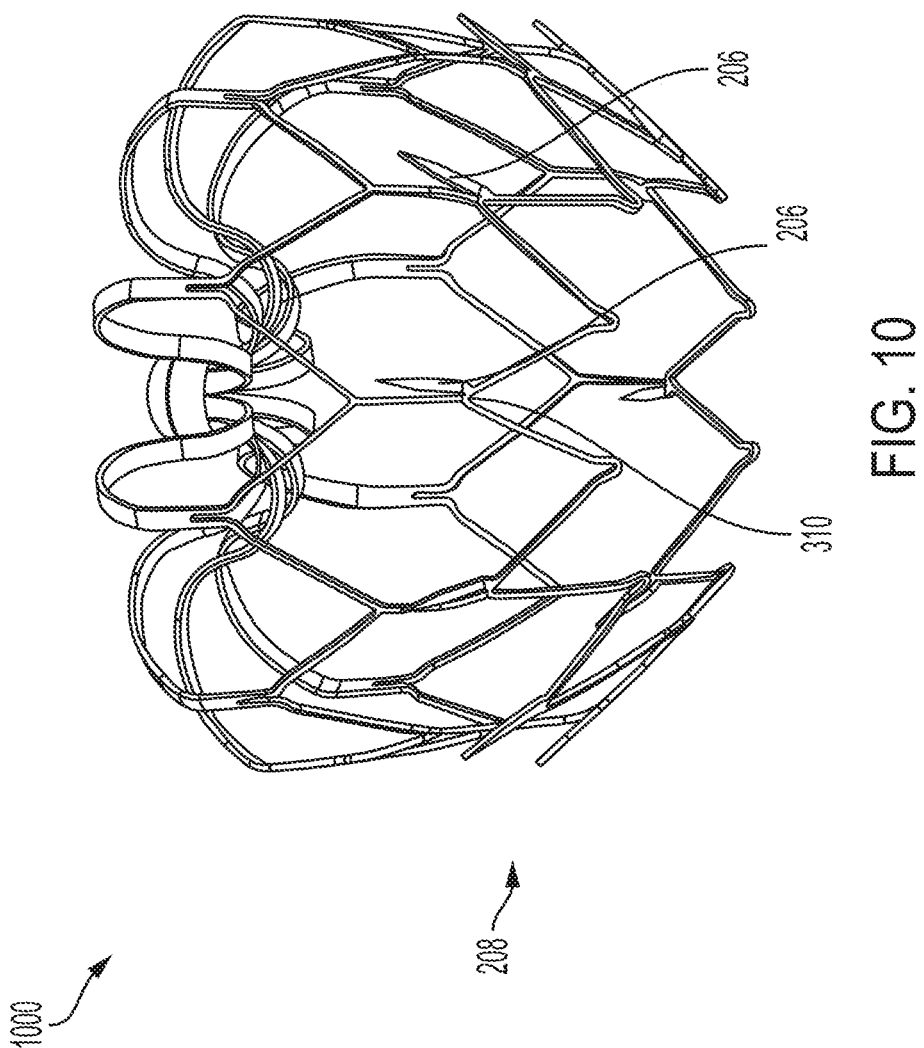
FIG. 10 shows another example frame for an implantable medical device, in accordance with various aspects of the disclosure.

FIG. 10 shows another example frame 1000 for an implantable medical device, in accordance with various aspects of the present disclosure. As shown in FIG. 10, the frame 1000 includes a different configuration than the frame 200 of FIG. 2 and the frame 200 of FIG. 4. Similar to the frame 200 of FIG. 2 and the frame 200 of FIG. 4, the frame 1000 includes a waist portion 208 and anchors 206 arranged at the waist portion 208. The waist portion 208 is located on the frame 1000 where the frame 1000 beings to taper toward its distal end. The anchors 206 are also arranged adjacent to junctions 310. The anchors 206 of FIG. 10 are side-saddle relative to the junctions 310.

In addition, the anchors 206 are configured to rotate inwardly in response to the frame 1000 being arranged in a delivery configuration. The waist portion 208 may act as a hinge to facilitate the anchors 206 being configured to rotate inwardly as discussed in further detail above.

Figure 11:
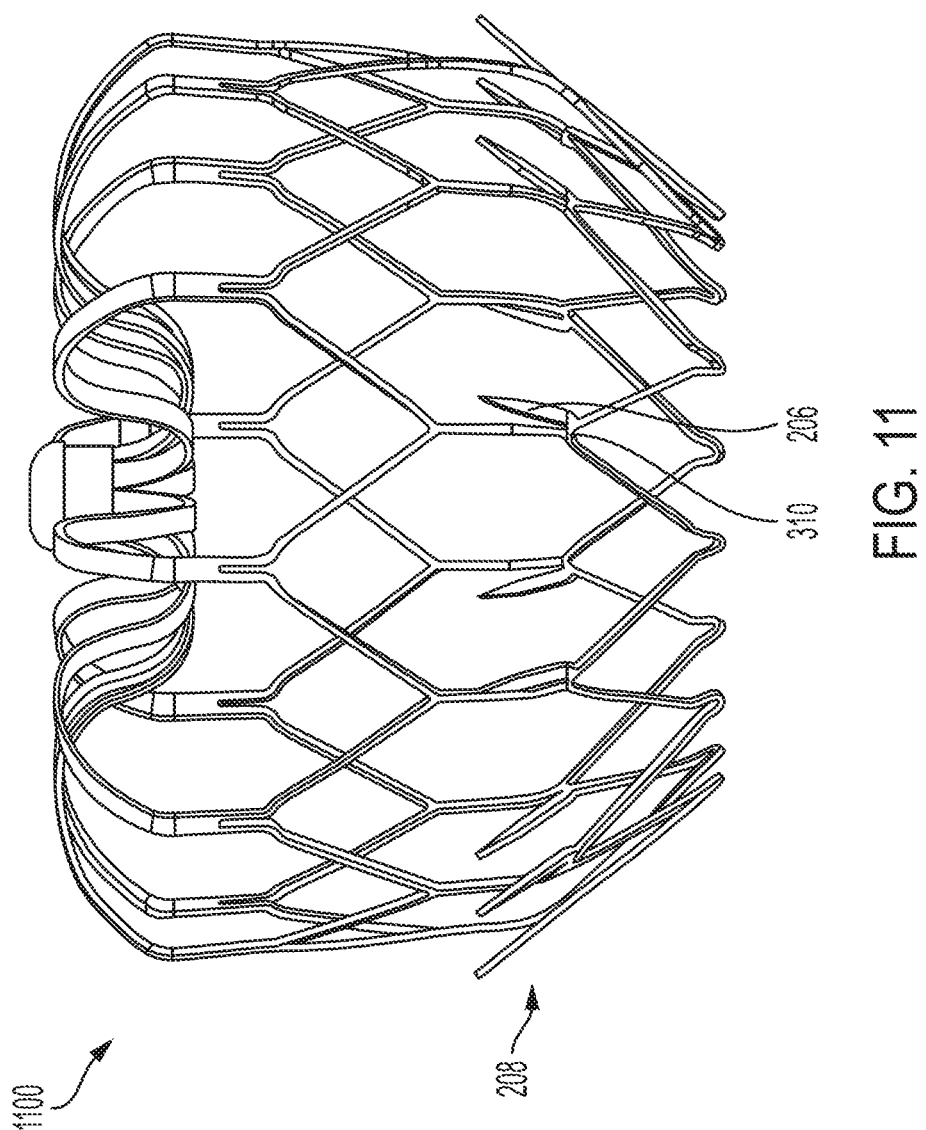
FIG. 11 shows another example frame for an implantable medical device, in accordance with various aspects of the disclosure.

FIG. 11 shows another example frame 1100 for an implantable medical device, in accordance with various aspects of the present disclosure. As shown in FIG. 11, the frame 1100 includes a different configuration that the frame 200 of FIG. 2 and the frame 200 of FIG. 4. Similar to the frame 200 of FIG. 2 and the frame 200 of FIG. 4, the frame 1100 includes a waist portion 208 and anchors 206 arranged at the waist portion 208. The waist portion 208 is located on the frame 1100 where the frame 1100 beings to taper toward its distal end. The anchors 206 are also arranged adjacent to the junctions 310. The anchors 206 of FIG. 11 are side-saddle relative to the junctions 310.

In addition, the anchors 206 are configured to rotate inwardly in response to the frame 900 being arranged in a delivery configuration. The waist portion 208 may act as a hinge to facilitate the anchors 206 being configured to rotate inwardly.

Figure 12:
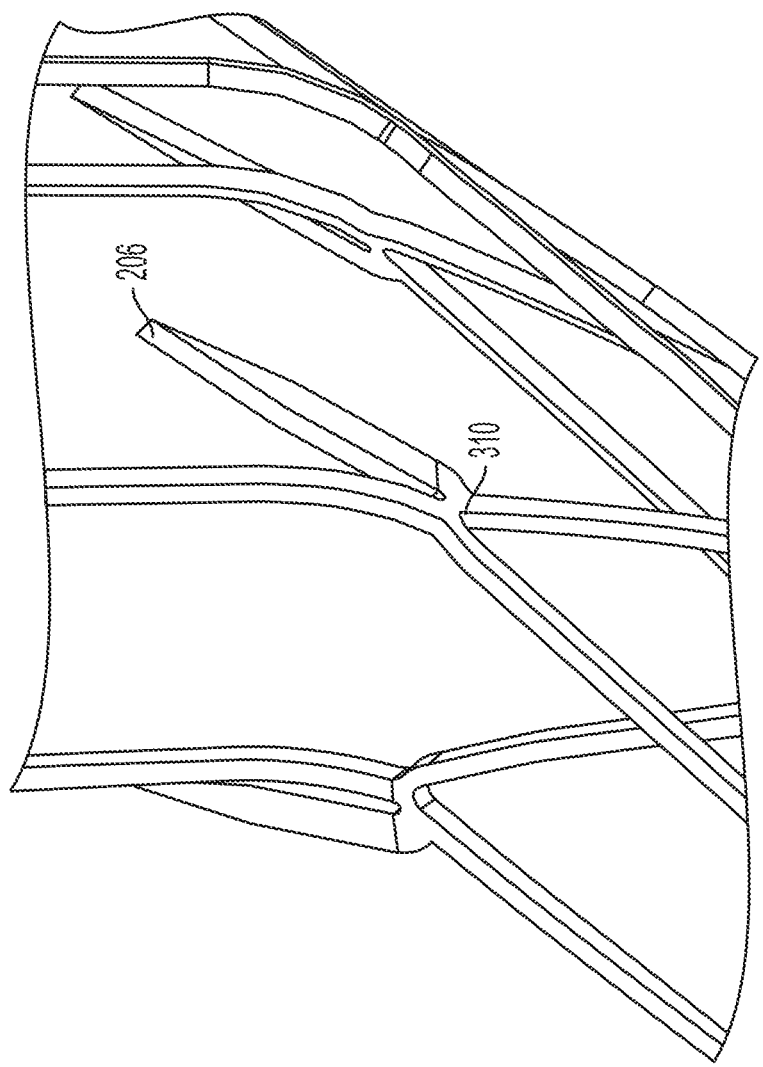
FIG. 12 shows a close-up view of an example anchor, as shown with the frames in FIGS. 10-11, in accordance with various aspects of the disclosure.

FIG. 12 shows a close-up view of an example anchor, as shown with the frames in FIGS. 9-10, in accordance with various aspects of the present disclosure.

The illustrative components shown in FIGS. 10-12 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 10-12 may be, in embodiments, integrated with various other components depicted therein (and/or components not illustrated), all of which are considered to be within the ambit of the disclosed subject matter. For example, the frames described with reference to FIGS. 1-6 may include side saddle anchors as shown in FIGS. 10-12.

FIG. 13A shows an example frame 1300 for an implantable medical device with anchors 1302 in a proximal-facing arrangement, in accordance with various aspects of the disclosure. The frame 1300 may form part of an implantable medical device such as a stent or stent graft. The anchors 1302 are arranged at a waist portion 1304 of the frame 1300. The waist portion 1304 is a portion of the frame 1300 that includes a curvature that alters an angle of the frame 1300 as shown in FIG. 13A. As also shown in FIG. 13A, the frame 1300 includes two curved portions: waist 1304 and portion 1306. The anchors 1302 may also be arranged at portion 1306. In certain embodiments, the frame 1300 includes anchors 1302 arranged at the waist 1304 and the portion 1306.

The anchors 1302 are configured to rotate inwardly in response to the frame 1300 being arranged in a delivery configuration. The waist portion 1304 (or portion 1306) may act as a hinge to facilitate the anchors 1302 being configured to rotate inwardly. The frame 1300 collapses inwardly when being arranged in the delivery configuration, and the waist portion 1304 may facilitate rotating of the one or more anchors 1302.

As shown in FIG. 13A, a root 1308 of the anchors 1302 is arranged at an end of the curvature of the waist 1306. The anchors 1302 may be configured to move inwardly (e.g., rotate) toward a longitudinal axis of the frame 1300 (e.g., by rotating) at the root 1308 in response to the frame 1300 being arranged in the delivery configuration. In collapsing the frame 1300 to a delivery configuration (e.g., elongation of the device to fit within a delivery catheter as shown in FIGS. 6A-B), the angle change or taper of the frame 1300 at the waist portion 1304 facilitates rotating of the anchors 1302 inwardly. Thus, the anchors 1302 are configured to rotate toward the longitudinal axis at the waist portion 1304 in response to the frame 1300 being arranged in the delivery configuration.

The anchors 1302 are in a proximal-facing arrangement relative to ends of the frame 1300. FIG. 13B shows the example frame for an implantable medical device 1300, shown in FIG. 13A, with anchors 1302 in a distal-facing arrangement, in accordance with various aspects of the disclosure. In either arrangement, the anchors 1302 are configured to rotate within the frame 1300.

Figure 14A:
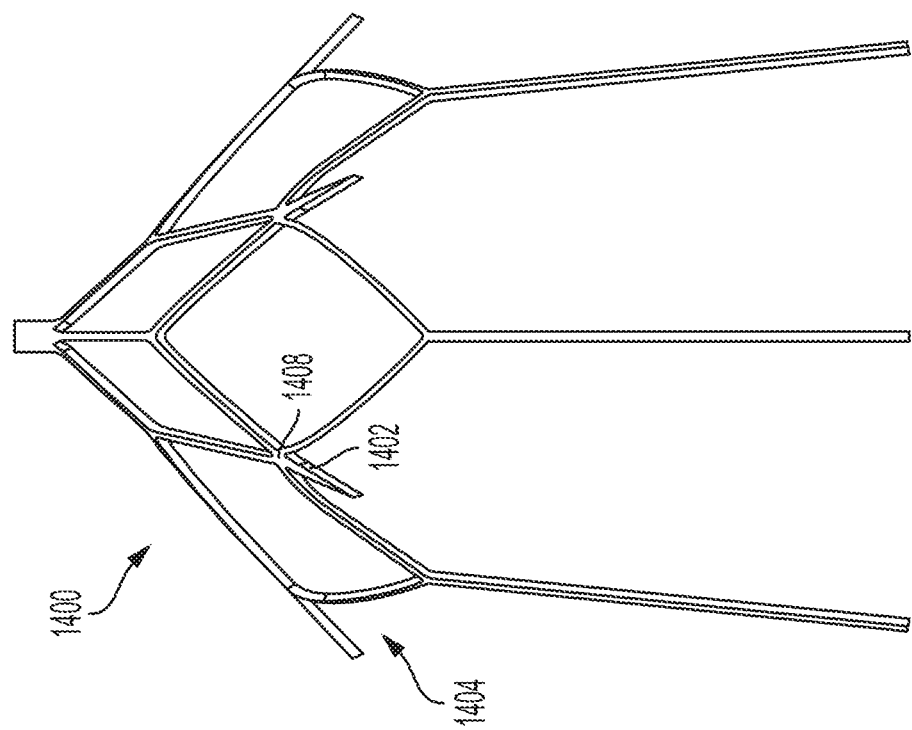
FIG. 14A shows another example frame for an implantable medical device with anchors in a proximal-facing arrangement, in accordance with various aspects of the disclosure.

FIG. 14A shows another example frame 1400 for an implantable medical device with anchors 1402 in a proximal-facing arrangement, in accordance with various aspects of the disclosure. The frame 1400 may form part of an implantable medical device such as a vena cava filter. The anchors 1402 are arranged at a waist portion 1404 of the frame 1400. The waist portion 1404 is a portion of the frame

1400 that includes a curvature that alters an angle of the frame 1400 as shown in FIG. 14A. The anchors 1402 are configured to rotate inwardly in response to the frame 1400 being arranged in a delivery configuration. The waist portion 1404 acts as a hinge to facilitate the anchors 1402 rotating. The frame 1400 collapses inwardly when being arranged in the delivery configuration, and the waist portion 1304 may facilitate rotating of the one or more anchors 1402.

As shown in FIG. 14A, a root 1408 of the anchors 1402 is arranged at an end of the curvature of the waist 1406. The anchors 1402 may be configured to move inwardly and rotate toward a longitudinal axis of the frame 1400 (e.g., by retracting or rotating) at the root 1408 in response to the frame 1400 being arranged in the delivery configuration. In collapsing the frame 1400 to a delivery configuration (e.g., elongation of the device to fit within a delivery catheter as shown in FIGS. 6A-B), the angle change or taper of the frame 1400 at the waist portion 1404 facilitates rotating of the anchors 1402 inwardly. Thus, the anchors 1402 are configured to rotate toward the longitudinal axis at the waist portion 1404 in response to the frame 1400 being arranged in the delivery configuration.

Figure 14B:
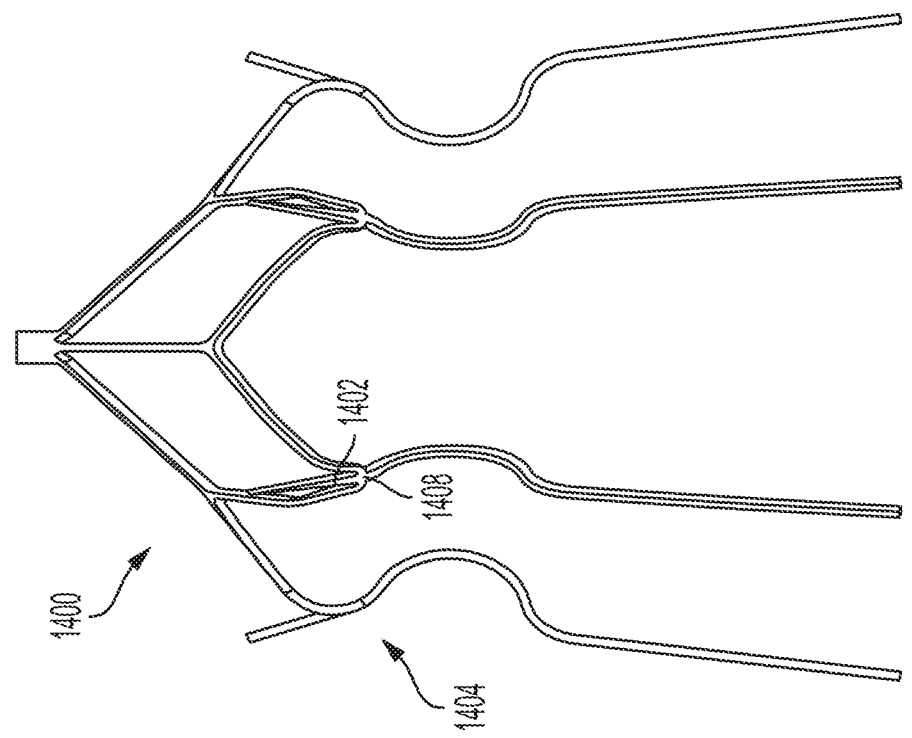
FIG. 14B shows the frame for an implantable medical device, shown in FIG. 14A, with anchors in a distal-facing arrangement, in accordance with various aspects of the disclosure.

The anchors 1402 are in a proximal-facing arrangement relative to ends of the frame 1400. FIG. 14B shows the example frame for an implantable medical device 1400, shown in FIG. 14A, with anchors 1402 in a distal-facing arrangement, in accordance with various aspects of the disclosure. In either arrangement, the anchors 1402 are configured to rotate within the frame 1400.

Figure 15:
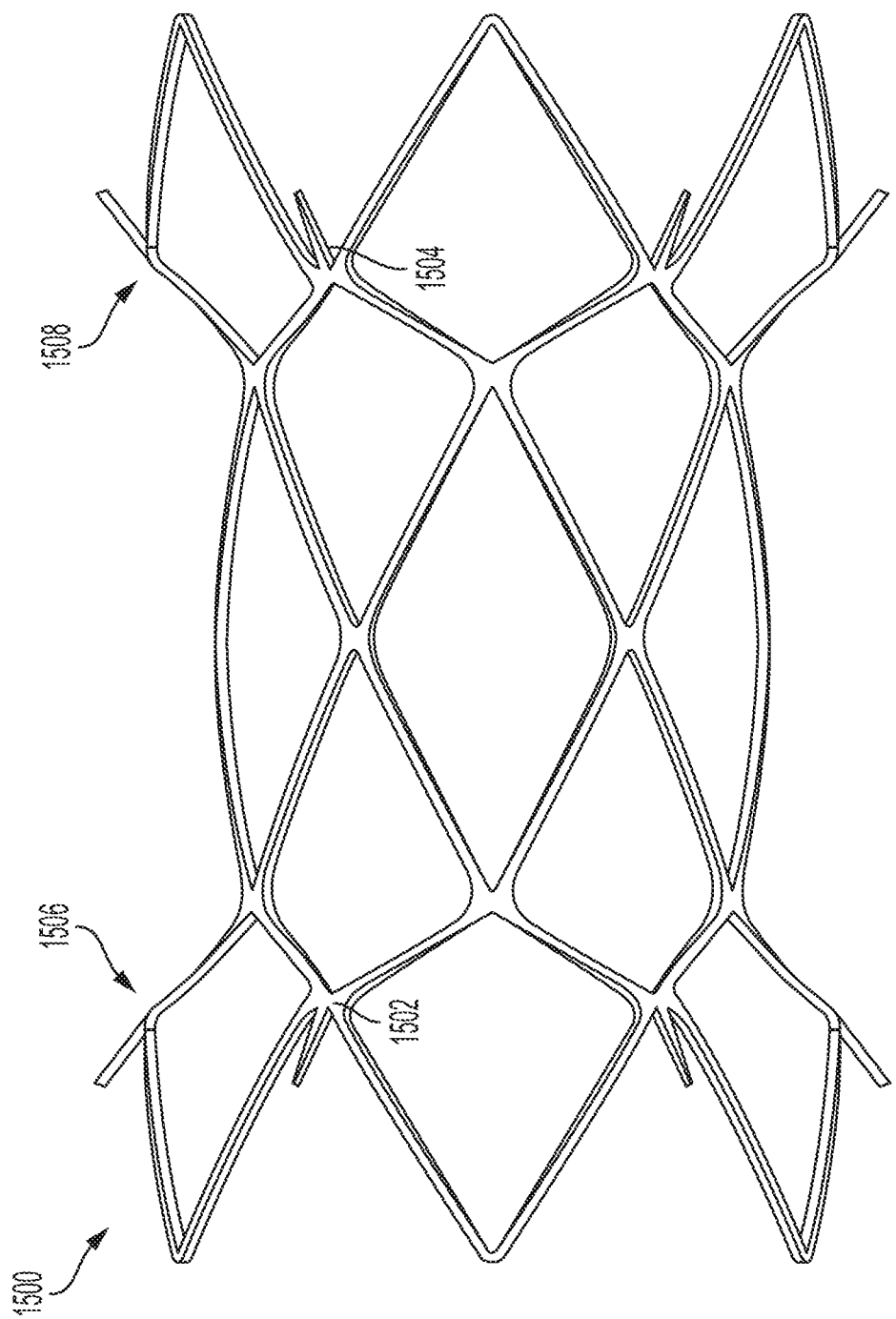
FIG. 15 shows an example frame for an implantable medical device with two sets of anchors, in accordance with various aspects of the disclosure.

FIG. 15 shows an example frame 1500 for an implantable medical device with two sets of anchors 1502, 1504, in accordance with various aspects of the disclosure. The frame 1500 may form part of an implantable medical device such as a stent or stent graft. The two sets of anchors 1502, 1504 are arranged at waist portions 1506, 1508 of the frame 1500. The waist portions 1506, 1508 are portions of the frame 1500 that includes a curvature that alters an angle of the frame 1500 as shown in FIG. 15.

The sets of anchors 1502, 1504 are configured to rotate inwardly in response to the frame 1500 being arranged in a delivery configuration. The waist portions 1506, 1508 may act as a hinge to facilitate the anchors 1502, 1504 being configured to rotate inwardly. The frame 1500 collapses inwardly when being arranged in the delivery configuration, and the waist portions 1506, 1508 may facilitate rotating of the anchors 1502, 1504.

Figure 16:
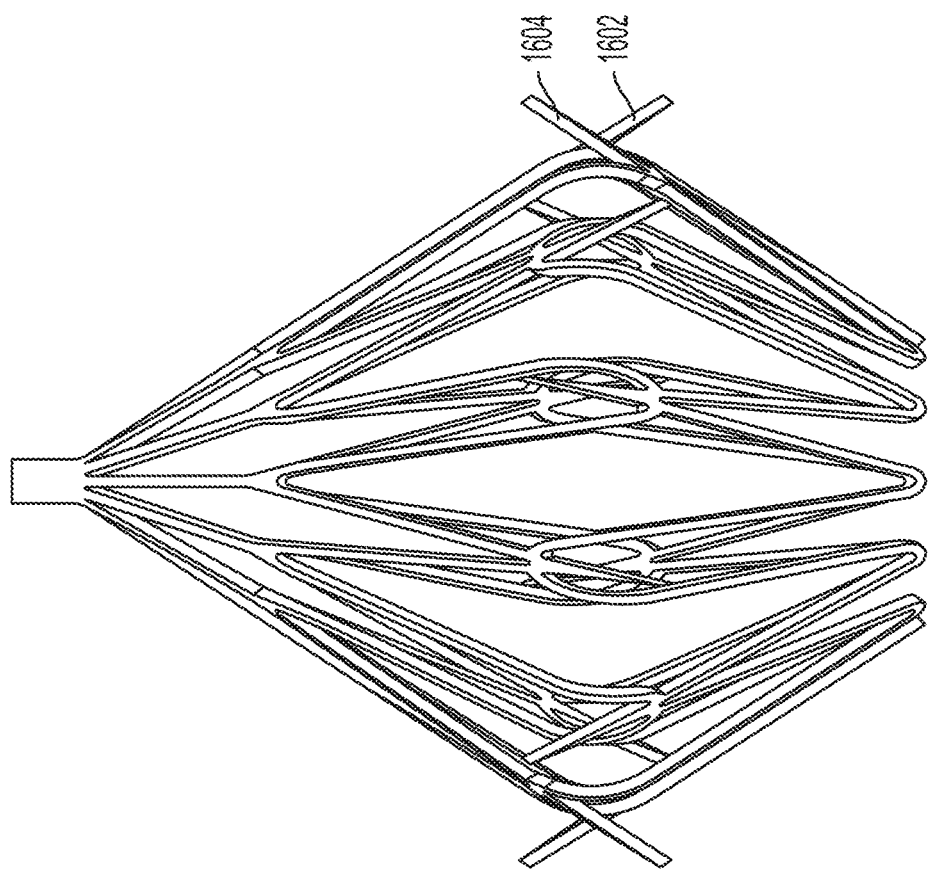
FIG. 16 shows an example frame for an implantable medical device with two sets of anchors, in accordance with various aspects of the disclosure.

FIG. 16 shows an example frame 1600 for an implantable medical device with two sets of anchors, in accordance with various aspects of the disclosure. The frame 1600 includes two sets of anchors 1602, 1604, in accordance with various aspects of the disclosure. The two sets of anchors 1602, 1604 face opposite ends of the frame 1600. The two sets of anchors 1602, 1604 are arranged at a waist portion 1606 of the frame 1600. The waist portion 1606 is characterized in that the waist portion 1606 includes a curvature that alters an angle of the frame 1600 as shown in FIG. 16.

The two sets of anchors 1602, 1604 are configured to rotate (or retract) inwardly in response to the frame 1600 being arranged in a delivery configuration. The waist portion 1606 may act as a hinge to facilitate the two sets of anchors 1602, 1604 being configured to rotate inwardly. The frame 1600 collapses inwardly when being arranged in the delivery configuration, and the waist portion 1606 may facilitate rotating of the two sets of anchors 1602, 1604.

Nitinol (NiTi) may be used as the material of the frames discussed herein. In other instances, the frames may be formed from other materials such as stainless steel, L605 steel, polymers, MP35N steel, polymeric materials, Pyhnox, Elgiloy, or any other appropriate biocompatible material, and combinations thereof, can be used as the material of the frames. The super-elastic properties and softness of NiTi may enhance the conformability of the frames. In addition, NiTi can be shape-set into a desired shape. That is, NiTi can be shape-set so that the frame tends to self-expand into a desired shape when the frames is unconstrained, such as when the frame is deployed out from a delivery system. More specifically, the frame (made of NiTi) may have a spring nature that allows the frame to be elastically collapsed or "crushed" to a low-profile delivery configuration for loading in a delivery system (e.g., as shown and discussed with reference to FIG. 1A and FIGS. 6A-B), and then to reconfigure to the expanded configuration, as shown in FIGS. 2 and 4, upon emergence from the delivery system. The frames, discussed herein, may be generally conformable, fatigue resistant, and elastic such that the frames may conform to the topography of the surrounding tissue when the occlusive device is deployed in a patient. In certain embodiments, bioresorbable or bioabsorbable materials may be used for the frame or a portion thereof, including for example, a bioresorbable or bioabsorbable polymer.

In certain instances, as shown in FIGS. 1A-C, a biocompatible material for a membrane may cover the frames discussed herein. In certain embodiments, the membrane may include a fluoropolymer, such as a polytetrafluoroethylene (PTFE) polymer or an expanded polytetrafluoroethylene (ePTFE) polymer. In some embodiments, the membrane may be formed of a polyester, a silicone, a urethane, a polyethylene terephthalate, or another biocompatible polymer, or combinations thereof. In some embodiments, bioresorbable or bioabsorbable materials may be used, for example a bioresorbable or bioabsorbable polymer. In some embodiments, the membrane can comprise a fluoropolymer, such as described in one or more of U.S. Pat. Nos. 7,049,380; 7,462,675; and 8,048,440, the contents of which are each incorporated by reference herein. In some embodiments, the membrane can comprise Dacron, polyolefins, carboxy methylcellulose fabrics, polyurethanes, or other woven or film elastomers. In some embodiments, the membrane can comprise knits or fibers. The membrane may be woven or non-woven in various embodiments including wires for example. In some embodiments, the membrane 70 may be formed of a combination and/or copolymer of fluoropolymers or blends thereof.

In some embodiments, the membrane is configured to inhibit, filter, modulate, or substantially modulate the passage of fluids and/or materials (such as blood and/or thrombus) through the membrane. In some embodiments, the membrane is configured to induce rapid tissue ingrowth therein. In an embodiment, the membrane provides for a blood or body fluid impermeable membrane that occludes the flow of blood or bodily fluids through the membrane yet promotes the ingrowth and endothelialization. The membrane can have a microporous structure that provides a tissue ingrowth scaffold for durable occlusion and supplemental anchoring strength of frames. In some embodiments, the membrane may be a porous member. Pores of the membrane may be sized to substantially, or in some examples completely, help prevent passage of blood, other bodily fluids, and emboli. In some implementations, the membrane prevents or substantially prevents passage of blood, other bodily fluids, thrombi, emboli, or other bodily materials through the membrane.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Several implantable occlusive device and frame embodiments have been described herein. It should be understood that one or more of the features described in the context of a particular device may be combined with one or more features of any other device or multiple devices described herein. That is, the features of the occlusive devices and frames described herein may be mixed and matched to provide hybrid occlusive device and device frame embodiments, and such hybrid occlusive device and device frame embodiments are within the scope of this disclosure. In some examples, one or more features described with respect to a particular device or frame may replace or be substituted for one or more features of another device or frame. In some examples, one or more features described with respect to a particular device or frame may be added to or included with another device or frame. Also, various combinations or sub-combinations of any of the features described herein may generally be used with any of the devices or frames described herein. It should be understood that the occlusive devices and occlusive device frames provided herein are scalable to a broad range of sizes so that the occlusive devices can be used in a variety of different anatomies, implant sites, and types of implementations.

Several characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. A device for placement in vessels, appendages, and openings in a body including a frame formed by a plurality of elongate members and having a proximal end, a distal end, and a longitudinal axis, the device comprising:
    an occlusive face arranged at the proximal end of the frame the occlusive face partially defined by struts extending radially toward the longitudinal axis;
    a first body portion having an outward curve extending distally from the occlusive face;
    a waist portion angled relative to the longitudinal axis;
    a second body portion tapering inwardly relative to the longitudinal axis toward the distal end; and
    one or more anchors arranged along the waist portion between adjacent elongate members of the frame converging at the waist portion and proximal to the second body portion, the one or more anchors being configured to rotate relative to and toward the longitudinal axis in response to the frame being arranged in a delivery configuration to avoid contact between an anchor tip and a delivery sheath and one or more roots of the one or more anchors includes a curvature with an angle between approximately 10 degrees to 55 degrees, relative to the longitudinal axis, in the deployed configuration.

2. The device of claim 1, wherein the waist portion is arranged between the first body portion and the second body portion and the one or more anchors are configured to rotate toward the longitudinal axis at the root in response to the frame being arranged in the delivery configuration.

3. The device of claim 2, wherein the first body portion or the second body portion includes circumferentially extending row of strut pairs with adjacent strut pairs joining together, each of the one or more anchors include a tip at a distal end, and the one or more anchors are configured to move inwardly and arrange the tip between the adjacent strut pairs in response to the frame being arranged in the delivery configuration.

4. The device of claim 1, wherein the one or more roots include a curvature with an angle between approximately −10 degrees to zero degrees, relative to the longitudinal axis, in the delivery configuration.

5. The device of claim 1, wherein the one or more anchors are configured to rotate toward the longitudinal axis at the waist portion in response to the frame being arranged in the delivery configuration.

6. The device of claim 5, wherein the waist portion includes a body angle relative to the first body portion and the second body portion, and the body angle facilitates rotation of the one or more anchors in response to the frame being arranged in the delivery configuration.

7. The device of claim 6, wherein the body angle is less than 180° in the deployed configuration.

8. The device of claim 7, wherein the one or more anchors include a radius in the deployed configuration that is less than or equal to a radius of the body angle.

9. The device of claim 1, wherein a flexibility of the second body portion is less than a flexibility of the waist portion.

10. A device for placement in vessels, appendages, and openings in a body having a delivery configuration and a deployed configuration, the device comprising:
    a frame having a proximal end, a distal end, and a longitudinal axis formed by a plurality of elongate members, the frame including:
        an occlusive face arranged at the proximal end of the frame, the occlusive face partially defined by struts extending radially toward the longitudinal axis;
        a first body portion including a plurality of cells and having an outward curve,
        a second body portion,
        a waist portion arranged between the first body portion and the second body portion and forming an angle of approximately between 20 degrees and 90 degrees between the first body portion and the second body portion, and at least one anchor having a root arranged at a distal end of the waist portion and a tip extending toward the proximal end and arranged between adjacent elongate members of the frame converging at the waist portion and arranged proximal to the second body portion, the at least one anchor projects outwardly relative to the longitudinal axis from the waist portion in the deployed configuration and nested within one or more of the plurality of cells in the delivery configuration.

11. The device of claim 10, wherein the at least one anchor is configured to rotate toward the longitudinal axis in response to the frame being arranged in the delivery configuration from the deployed configuration.

12. The device of claim 10, wherein the at least one anchor is configured to rotate relative to the longitudinal axis and move outwardly the anchor tip in response to the frame being arranged in the deployed configuration from the delivery configuration.

13. The device of claim 10, wherein the root of each of the at least one anchor is located approximately at 40% of a total device length from the distal end of the frame.

14. The device of claim 10, wherein at least one of a flexibility of the first body portion and a flexibility of the second body portion is less than a flexibility of the waist portion.

15. The device of claim 10, wherein widths of adjacent elongated members are reduced adjacent to the at least one anchor.

16. A system for deployment of a device in vessels, appendages, and openings in a body, the system comprising:
a delivery catheter having a lumen and substantially circular body portion; and
a frame having a proximal end, a distal end, and a longitudinal axis formed by a plurality of elongate members, the frame including:
an occlusive face arranged at the proximal end of the frame the occlusive face partially defined by struts extending radially toward the longitudinal axis is inserted after "the frame";
a first body portion having an outward curve extending distally from the occlusive face;
a second body portion tapering inwardly relative to the longitudinal axis toward the distal end;
a waist portion arranged between the first body portion and the second body portion; and
one or more anchors arranged along the waist portion and proximal to the second body portion, the one or more anchors being configured to move inwardly relative to and toward the longitudinal axis in response to the frame being arranged within the delivery catheter to avoid contact between an anchor tip and the delivery catheter and arranged between adjacent elongate members of the frame converging at the waist portion.

17. The system of claim 16, wherein the one or more anchors are configured to rotate toward the longitudinal axis without contacting the substantially circular body portion in response to being arranged within the delivery catheter.

18. The system of claim 16, wherein the one or more anchors are configured to move outwardly relative to the longitudinal axis in response to deploying the frame from the delivery catheter.

19. The system of claim 16, wherein the delivery catheter is configured to deploy the distal end of the frame prior to the proximal end of the frame, and the one or more anchors project outwardly from the waist portion and curve upward toward the proximal end in response to deploying the frame from the delivery catheter in a deployed configuration.

20. The system of claim 16, wherein the delivery catheter is configured to recapture the frame from a deployed configuration and rotate the one or more anchors toward the longitudinal axis in response to drawing the frame into the delivery catheter.

21. A method for deploying a device in vessels, appendages, and openings in a body, the method comprising:
arranging an implantable medical device for delivery formed by a frame having a proximal end, a distal end, a longitudinal axis and a plurality of elongate members, the implantable medical device having an occlusive face arranged at the proximal end of the frame and partially defined by struts extending radially toward the longitudinal axis, a first body portion having an outward curve extending distally from the occlusive face, a second body portion tapering inwardly relative to the longitudinal axis toward the distal end, a waist portion arranged between the first body portion and the second body portion, and one or more anchors arranged along the waist portion proximal to the second body portion;
collapsing the device by loading device into a delivery catheter whereby the one or more anchors move inwardly toward the longitudinal axis in response to the frame being arranged within the delivery catheter; and
implanting the device within the body by deploying the device from the delivery catheter and expanding the frame to a deployed configuration with the one or more anchors being configured to move radially outward from the longitudinal axis and engage tissue in the body and arranged between adjacent elongate members of the frame converging at the waist portion.

22. The method of claim 21, further comprising reloading the device into the delivery catheter, after implanting the device, to disengage the one or more anchors from the tissue and rotate the one or more anchors toward the longitudinal axis.

23. The method of claim 22, further comprising re-implanting the device within the body, after reloading the device into the delivery catheter, with the one or more anchors being configured to rotate radially outward from the longitudinal axis and engage tissue in the body.

* * * * *